United States Patent
Kaplan et al.

(10) Patent No.: US 12,403,176 B2
(45) Date of Patent: Sep. 2, 2025

(54) HYDROPHOBIC SILK FIBROIN COMPOSITIONS AND METHODS OF MAKING THE SAME

(71) Applicant: Trustees of Tufts College, Medford, MA (US)

(72) Inventors: David L. Kaplan, Concord, MA (US); Krishna Kumar, Cambridge, MA (US); Vittorio Montanari, Medford, MA (US); Morgan Hawker, Clovis, CA (US); Julia Fountain, Medford, MA (US); Junqi Wu, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 533 days.

(21) Appl. No.: 17/907,404

(22) PCT Filed: Mar. 25, 2021

(86) PCT No.: PCT/US2021/024253
§ 371 (c)(1),
(2) Date: Sep. 26, 2022

(87) PCT Pub. No.: WO2021/195445
PCT Pub. Date: Sep. 30, 2021

(65) Prior Publication Data
US 2023/0123989 A1    Apr. 20, 2023

Related U.S. Application Data

(60) Provisional application No. 62/994,618, filed on Mar. 25, 2020.

(51) Int. Cl.
A61K 38/17    (2006.01)
C08H 1/00    (2006.01)
C08L 89/00    (2006.01)

(52) U.S. Cl.
CPC .......... *A61K 38/1767* (2013.01); *C08H 1/00* (2013.01); *C08L 89/00* (2013.01)

(58) Field of Classification Search
CPC ........ C08H 1/00; C08L 89/00; A61K 38/1767
See application file for complete search history.

(56) References Cited

U.S. PATENT DOCUMENTS

| | | |
|---|---|---|
| 2008/0275216 A1 | 11/2008 | Kumar et al. |
| 2018/0361015 A1 | 12/2018 | Burke et al. |
| 2019/0055279 A1 | 2/2019 | Kumar et al. |

FOREIGN PATENT DOCUMENTS

| | | |
|---|---|---|
| CN | 108976450 A | 12/2018 |
| WO | 2017192227 A1 | 11/2017 |
| WO | 2021195445 A1 | 9/2021 |

OTHER PUBLICATIONS

PCT/US2021/024253, "International Application Serial No. PCT/US2021/024253, International Preliminary Report on Patentability mailed Sep. 22, 2022", Tufts University, 7 pages.
PCT/US2021/024253, "International Application Serial No. PCT/US2021/024253, International Search Report and Written Opinion mailed Jul. 8, 2021", Tufts University, 9 pages.

*Primary Examiner* — Jafar F Parsa
(74) *Attorney, Agent, or Firm* — GTC Law Group PC & Affiliates

(57) ABSTRACT

The present disclosure relates to compositions, methods of making, and methods of using a modified silk-based composition having a selectively tunable hydrophobicity. The provided compositions include silk fibroin having a haloalkyl substituent. The haloalkyl substituent is coupled to an amino acid of the silk fibroin though a linking agent.

20 Claims, 10 Drawing Sheets

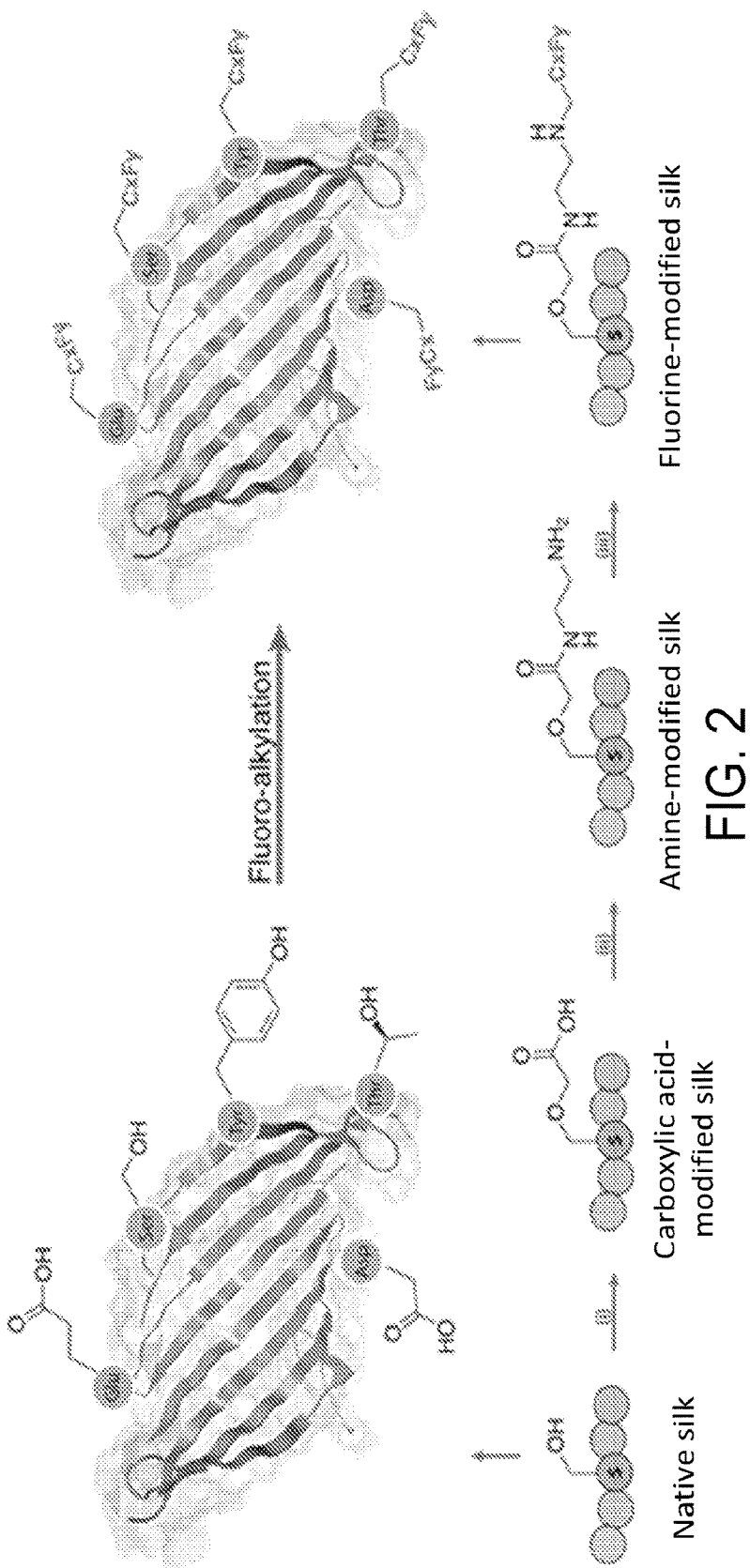
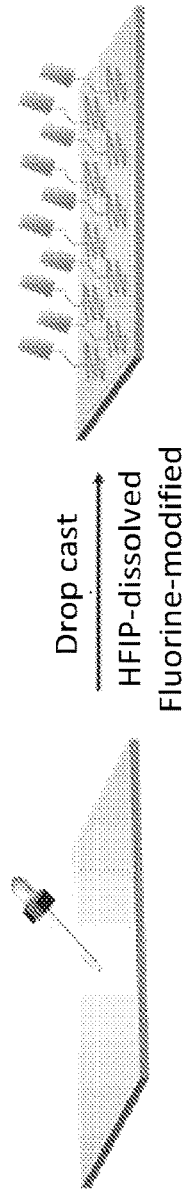
FIG. 2
FIG. 3

| Name | Structure |
|---|---|
| C2 | 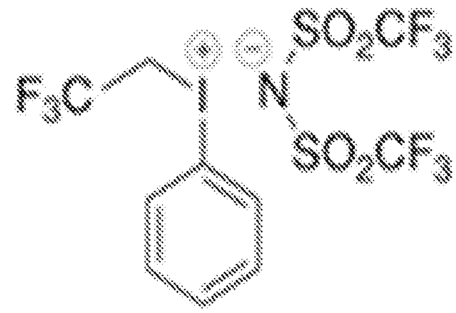 |
| C4 | 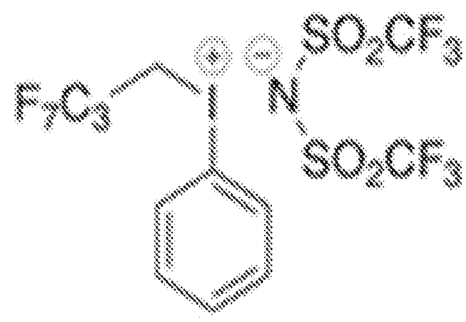 |
| C8 | 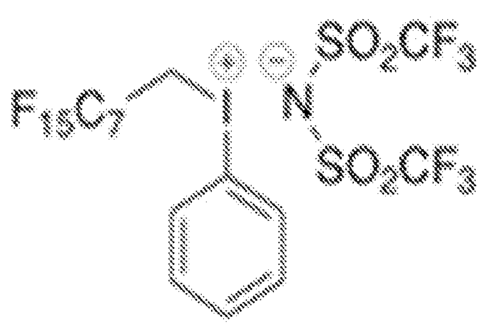 |
| C9 | 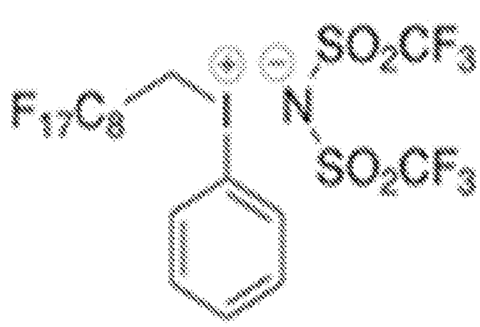 |

HYDROPHOBIC SILK FIBROIN COMPOSITIONS AND METHODS OF MAKING THE SAME

CROSS-REFERENCE TO RELATED APPLICATIONS

This application is the national stage entry of PCT/US2021/024253, filed Mar. 25, 2021, which is related to, and claims priority to U.S. Provisional Patent Application No. 62/994,618, filed Mar. 25, 2020. The contents of these applications are incorporated by reference herein.

STATEMENT REGARDING FEDERALLY SPONSORED RESEARCH

This invention was made with government support under grant FA9550-17-1-0333 awarded by the United States Air Force. The government has certain rights in the invention.

BACKGROUND

Biomaterials composed of silk fibroin hold a promising future in medicine, with applications ranging from wound dressings to bioelectronics. The limited immunogenic response and broad cytocompatiblity make silk an excellent candidate for biomedical use. Silk has exceptional mechanical properties (e.g., tensile strength >700 MPa), and the ability to control degradation through modulating the secondary structure of the protein allow silk to be easily transformed into a variety of architectures such as films, microparticles, and scaffolds with complex three-dimensional geometries. These characteristics make silk a versatile base for a myriad biomaterials. The challenge of modulating specific interactions at the interface of silk constructs and surrounding biological environments, however, must be met to realize the full utility of this material. A silk-based system with tunable chemical properties is necessary to address this challenge because the silk surface chemistry directly influences interfacial interactions.

Multiple approaches to chemically-modify silk have been developed thus far. These methods have attempted to overcome the synthetic challenges associated with silk, namely its composition of non-reactive glycine (45.9 mol %) and alanine (30.3 mol %) residues. To this end, the majority of synthetic methods have targeted amino acid residues that are easily amenable to modification, including serine (12.1 mol %), threonine (0.9 mol %), tyrosine (5.3 mol %), aspartic acid (0.5 mol %), and glutamic acid (0.6 mol %). Previous synthetic approaches have introduced functional groups that promote a specific response from a biological system, with a major focus on enhancing cell attachment and adhesion. As one example, poly-D, L-lactic acid has been conjugated to silk to extend proliferation and confluency of osteoblasts in vitro. Although cell attachment is key for certain applications of silk-based biomaterials (e.g., tissue engineering), interactions that prevent adhesion of biological species are of equal importance. For many biomedical devices, interaction with certain cell types and/or bacteria can inhibit the device function, as is the case for stents, wound dressings, and catheters.

Developing a method to fabricate silk-based materials that prevent biomolecule attachment would have high utility in such aforementioned applications.

SUMMARY

The present disclosure addresses the aforementioned drawbacks by providing a modified silk-based composition having a selectively tunable hydrophobicity. In some embodiments, provided herein is a composition including silk fibroin having a haloalkyl substituent, and a linking agent that couples the haloalkyl substituent to a select set of amino acids within the silk fibroin.

In other embodiments, the present disclosure provides a method for making a modified silk having a predetermined hydrophobicity. The method includes designing or selecting one or more haloalkyl substituent and selecting a substitution pattern of the one or more haloalkyl substituents in order to produce the predetermined hydrophobicity. The method further includes making the modified silk having the substitution pattern of the one or more haloalkyl substituents.

DESCRIPTION OF THE DRAWINGS

FIG. 2 is a schematic overview of synthesis of fluorinated silk films, in accordance with aspects of the present disclosure. (i) a. NaOH, $H_2O$. pH 13 b. $ClCH_2COOH$ (ii) a. NaOH. $H_2O$, pH 5.5 b. EDC, MES buffer, c. $H_2N(CH_2)_2NH_2$, MES Buffer, d. pH>10.5 (iii) Iodonium Salt, $Ch_2Cl_2$, b. Lutidine, $CH_2Cl_2$. The hydroxyls of serine and other residues were alkylated to introduce carboxylic acid functionality, and then treated under standard diazonium coupling conditions to install a primary amine group. A trivalent iodonium salt was then used to couple the fluorocarbon chain to the free amine. pdb: 3UA0.

FIG. 3 is an illustration of a method of making a solid form material from a fluorinated silk fibroin solution, in accordance with aspects of the present disclosure. The material resulting from the reactions illustrated in FIG. 2 was dissolved in hexafluoroisopropanol (HFIP) and drop cast onto a glass slide.

DETAILED DESCRIPTION

Figure 1:
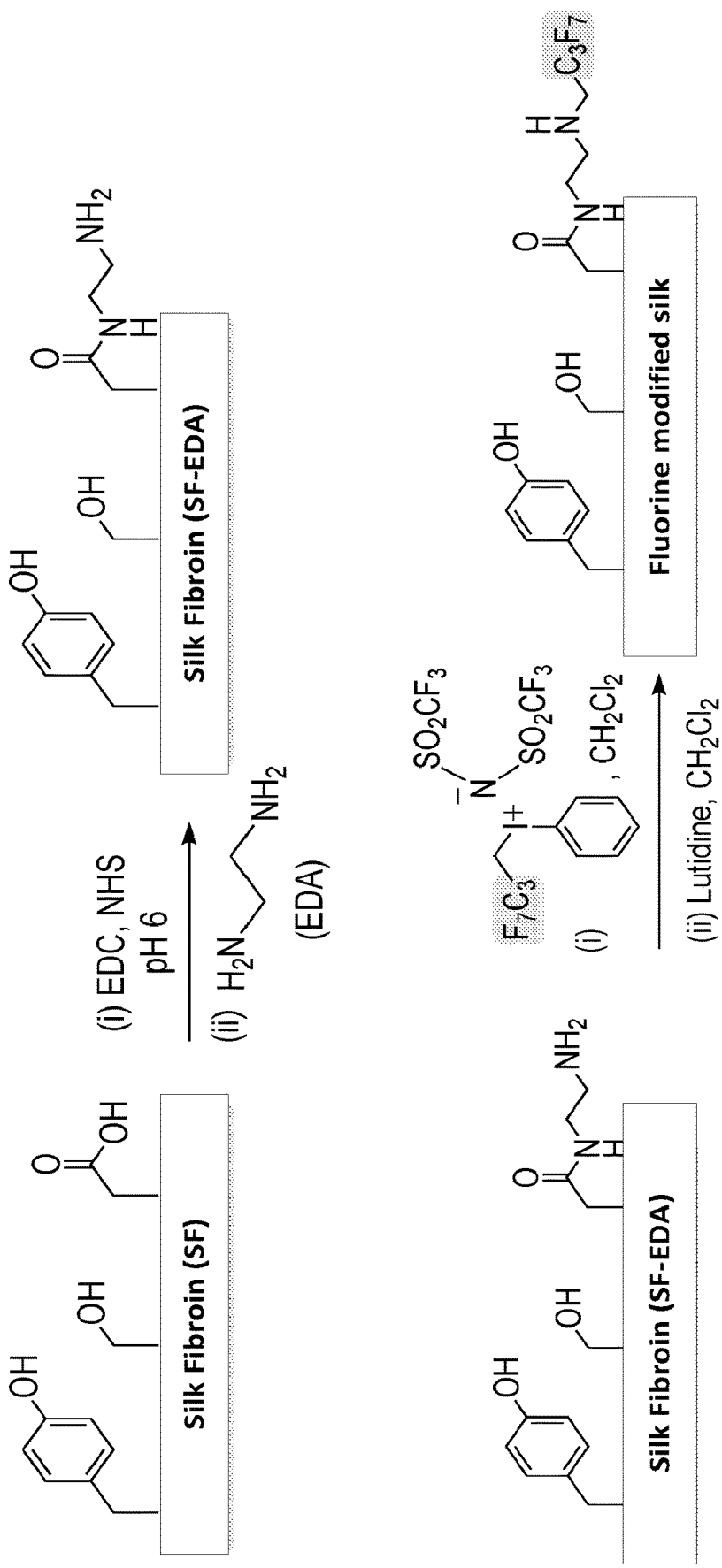
FIG. 1 illustrates an exemplary reaction scheme, in accordance with aspects of the present disclosure.
Figure 1:
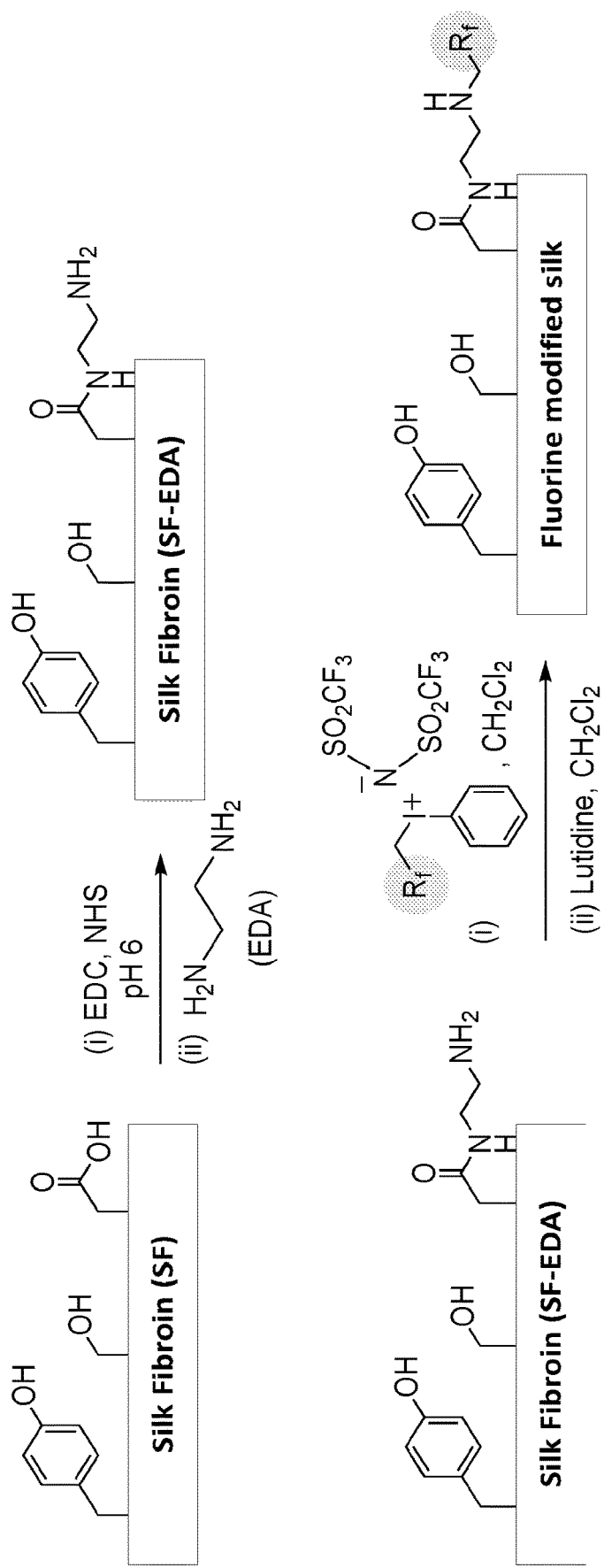

Before the present invention is described in further detail, it is to be understood that the invention is not limited to the particular embodiments described. It is also understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10.

Described herein are compositions and methods of making modified silk compositions having a selectively tunable hydrophobicity. In some embodiments, the silk fibroin compositions may be omniphobic. As used herein, the term "omniphobic" may refer to a composition that repels both hydrophilic solvents (e.g., water) and hydrophobic solvents (e.g., oils), as well as other materials including, but not limited to, colloids and dirt.

Conventional methods to append chemical functionalities to silk fibroin typically include incorporating modifications that promote cell attachment. An equally important physiochemical property is to enhance anti-adhesion, non-stick, or non-reactive properties to a biomaterial. These characteristics can be used to prevent fouling or control swelling of the material. The modified silk compositions described herein may be dissolvable in organic solvents, such as hexafluoroisopropanol (HFIP), which adds to the number of possible manufacturing methods. The solubility in organic solvents, such as HFIP, allows for the modified silk to be used in a wide range of applications such as hydrophobic inks and coatings which may be useful in modulating the attachment of unwanted cells and other biological materials to implantable biomedical devices like stents and catheters. One non-limiting example application of a modified silk coating would be using the hydrophobic coating in the shipping industry to prevent the attachment of barnacles to ships. In some embodiments, the modified silk compositions described herein may be used to control the swelling of silk screws used in bone repair due to the uptake of water. Other applications may be in breathable silk-based non-wetting materials.

Modified Silk Compositions:

In some embodiments, the modified silk composition includes silk comprising a haloalkyl substituent and a linking agent that couples the haloalkyl substituent to an amino acid of the silk fibroin.

The composition can be in the form of a solution. The composition can have a solid form. Many of the most unexpected results, including the improved hydrophobicity and the reduced water uptake, are associated only with the solid form.

As used herein, the term "silk fibroin" refers to silk fibroin protein whether produced by silkworm, spider, or other insect, or otherwise generated (Lucas et al., Adv. Protein Chem., 13: 107-242 (1958)). Any type of silk fibroin can be used in different embodiments described herein. Silk fibroin produced by silkworms, such as *Bombyx mori*, is the most common and represents an earth-friendly, renewable resource. For instance, silk fibroin used in a silk film may be attained by extracting sericin from the cocoons of *B. mori*. Organic silkworm cocoons are also commercially available. There are many different silks, however, including spider silk (e.g., obtained from Nephila clavipes), transgenic silks, genetically engineered silks, such as silks from bacteria, yeast, mammalian cells, transgenic animals, or transgenic plants, and variants thereof, that can be used. See, e.g., WO 97/08315 and U.S. Pat. No. 5,245,012, each of which is incorporated herein by reference in their entireties.

In some embodiments, the modified silk composition includes a haloalkyl substituent. As used herein, the term "halo" or "halo substituent" may refer to a halogen substituent in a chemical compound, such as fluoro (which may be depicted as —F), bromo (which may be depicted as —Br), chloro (which may be depicted as —Cl), and iodo (which may be depicted as —I). As used herein, the term "alkyl" or "alkyl substituent" may refer to a linear or branched-chain saturated hydrocarbyl substituent (i.e., a substituent obtained from a hydrocarbon by removal of a hydrogen). In some embodiments, the alkyl substituent contains from one to twenty carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like. Other chemical terms shall be given their common meaning under IUPAC definitions.

In some embodiments, the haloalkyl substituent comprises a structure of $-C_xH_{0-2}R_{0-3}$, where x ranges from 1 to 20 carbon atoms and R is one or more halo substituent selected from the group consisting of fluoro, chloro, bromo, and iodo. In some embodiments, x is greater than 2 carbon atoms, is greater than 3 carbon atoms, is greater than 4 carbon atoms, is greater than 5 carbon atoms, or is greater than 6 carbon atoms. In some embodiments, x is less than 7 carbon atoms, or is less than 8 carbons atoms, is less than 9 carbon atoms, or is less than 10 carbon atoms, or is less than 11 carbon atoms, or is less than 12 carbon atoms, or is less than 13 carbon atoms, or is less than 14 carbon atoms, or is less than 15 carbon atoms, or is less than 16 carbon atoms, or is less than 17 carbon atoms, or is less than 18 carbon atoms, or is less than 19 carbon atoms, or is less than 20 carbon atoms. In some embodiments, x ranges from one to four carbon atoms, or from one to five, or from one to six, or from one to seven, or from one to eight, or from one to nine, or from one to ten carbon atoms.

In some embodiments, a linking agent couples the haloalkyl substituent to an amino acid of the silk fibroin. As used herein, the term "linking agent" may refer to one or more chemical moiety that covalently attaches the haloalkyl substituent to an amino acid in the silk fibroin. In some embodiments, the linking agent includes one or more chemical moiety selected from the group consisting of a sulfonic acid group, a carboxylic acid group, an amine group, a diamine a ketone group, an alkyl group, an alkoxy group, a thiol group, a disulfide group, a nitro group, an aromatic group, an ester group, an amide group, and a hydroxyl group. In some embodiments, the linking agent is a covalent bond that directly attaches the haloalkyl substituent to the silk fibroin. In some embodiments, the link agent is covalently attached to an amino acid in silk fibroin comprising a hydroxyl substituent, such as serine, threonine, tyrosine, aspartic acid, and glutamic acid.

In some embodiments, the linking agent is covalently bonded to the hydroxyl substituent of the amino acid in silk fibroin, and comprises a structure of —$R_1(CO)(NR_2R_3)R_4(NR_5R_6)X$, where $R_1$ comprises $C_1$-$C_6$ alkyl, $R_2$ comprises a $C_1$-$C_{10}$ alkyl, $R_3$ comprises hydrogen, a $C_1$-$C_{10}$ alkyl, or an aryl group, $R_4$ comprises a $C_1$-$C_{10}$ alkyl, $R_5$ comprises a $C_1$-$C_{10}$ alkyl, $R_6$ comprises hydrogen or a $C_1$-$C_{10}$ alkyl, and X comprises the haloalkyl substituent.

In some embodiments, the modified silk in a solid form has a water contact angle from 50° to 150°, or greater. In some embodiments the modified silk has a water contact angle greater than 50°, or greater than 60°, or greater than 70°, or greater than 80°, or greater than 90°, or greater than 100°, or greater than 110°, or greater than 120°. In some embodiments, the modified silk has a water contact angle of less than 130°, or less than 140°, or less than 150°. The water contact angle (WCA) may be determined using a goniometer by depositing 2-7 uL drop of ultrapure water on the surface of the modified silk. The resulting drop profile may be fit using software (e.g., DROPimage Advanced Software) to determine the WCA using known methods, such as the Young equation or other suitable known techniques.

In some embodiments, the modified silk has a halo content from 20 atomic percentage (at. %) to 50 at. %, as determined by X-ray photoelectron spectroscopy (XPS). In some embodiments, the modified silk has a halo content of greater than 20 at. %, or greater than 25 at. %, or greater than 30 at. %, or greater than 35 at. %. In some embodiments, the modified silk has a halo content of less than 40 at. %, or less than 45 at. %, or less than 50 at. %.

In some embodiments, the modified silk has a primary amine content that ranges from 0 to 0.7 mM. In some embodiments, the modified silk has a primary amine content of less than 0.7 mM, or less than 0.6 mM, or less than 0.5 mM, or less than 0.4 mM, or less than 0.3 mM, or less than 0.2 mM, or less than 0.1 mM. The primary amine content may be determined by a ninhydrin quantification. It should be appreciated that the change/reduction in primary amine content is representative of the degree of modification by the one or more haloalkyl substituents.

In some embodiments, the modified silk may be formed into a coating deposited on a substrate. In some embodiments, the coating may have a thickness of 100 μm to 50 mm, or greater. In some embodiments, the modified silk may be formed, manufactured, or shaped into a biomedical device including, but not limited to, a screw (e.g., for bone repair), a stent, or a catheter. In some embodiments, the modified silk may be formed into an ink solution for use in printing applications (e.g., inkjet printing, screen printing, 3D printing). In some cases, the modified silk may be used in a multi-component braided material type application. In some cases, the modified silk may be used in a dual-coated surface, where one side is hydrophobic and the other side has a different hydrophobicity. In some cases, the modified silk may be used in electronic devices. In some cases, the modified silk may be used as a self-cleaning surface coating for piping and/or metal conduits. In some cases, the modified silk may be used in a textile application to modulate water uptake, transport, cleaning, or the like. In some cases, the modified silk forms a pattern within a broader silk material by surface modifying the broader silk material in a predetermined pattern. In some cases, the modified silk may be used in water repellant devices. In some cases, the modified silk may be used in applications for the reduction of biofouling. In some cases, the modified silk may be used in materials that are intended to contact food, in order to control freshness, water content, contamination from organisms, and the like.

In some cases, the one or more haloalkyl substituents are distributed substantially homogeneously throughout the modified silk and/or the solid form. As used herein, "substantially homogeneous" refers to the distribution of the one or more haloalkyl substituents within a bulk material and not the distribution within the silk fibroin protein itself, and refers to a distribution where the variance is no more and no less than 50% throughout the composition.

As used herein, "heterogeneously" refers to any distribution that is not substantially homogenous".

In some cases, the one or more haloalkyl substituents are distributed heterogeneously where the haloalkyl content is high at or near the surface of a solid form of modified silk and the haloalkyl content is low at an interior portion of the solid form.

For clarity, features described in this section are combinable with features described in the following section, without limitation unless the context clearly dictates otherwise (e.g., a water contact angle is not combinable with an aqueous solution embodiment).

Method of Forming the Modified Silk:

The present disclosure provides a method for making a modified silk having a predetermined hydrophobicity. In some embodiments, the method includes designing and/or selecting one or more haloalkyl substituents and selecting a substitution pattern of the one or more haloalkyl substituents in order to produce the predetermined hydrophobicity. The method further includes making the modified silk having the substitution pattern of the one or more haloalkyl substituents. The predetermined hydrophobicity can be associated with a given reduction in water uptake. The predetermined hydrophobicity can be associated with reduced cell adhesion.

Referring to FIG. 1, an exemplary fluorination reaction scheme (top) and an exemplary haloalkylination reaction scheme (bottom) are shown.

In some embodiments, silk fibroin solution can be prepared by any conventional method known to one skilled in the art. In some embodiments, a silk solution is an aqueous silk solution. In some embodiments, silk polypeptide compositions utilized in accordance with the present invention are substantially free of sericins (e.g., contain no detectable sericin or contain sericin at a level that one of ordinary skill in the pertinent art will consider negligible for a particular use).

For example, B. mori cocoons are boiled for about 30 minutes in an aqueous solution. In some embodiments, the aqueous solution is about 0.02M $Na_2CO_3$. In some embodiments, boiling (degumming) time is in a range of about 5 minutes to about 120 minutes. In some embodiments, boiling (degumming) temperature is in a range of about 30° C. to about 120° C. In some embodiments, boiling (degumming) may occur under pressure. For example, suitable pressures under which protein fragments can be produced may range between about 10 to 40 psi.

The cocoons may be rinsed, for example, with water to extract the sericin proteins and the extracted silk is dissolved in an aqueous salt solution. Exemplary salts useful for this purpose include lithium bromide, lithium thiocyanate, calcium nitrate or other chemicals capable of solubilizing silk. Preferably, in some embodiments, the extracted silk is dissolved in about 9-12 M LiBr solution. The salt is consequently removed using, for example, dialysis.

In some embodiments, making the modified silk includes coupling a linking agent to an amino acid of the silk fibroin, for example, via a hydroxyl substituent on the amino acid. The linking agent may comprise one or more chemical moiety selected from a sulfonic acid group, a carboxylic acid group, an amine group, a ketone group, an alkyl group, an alkoxy group, a thiol group, a disulfide group, a nitro group, an aromatic group, an ester group, an amide group, and a hydroxyl group.

In some embodiments, the linking agent is formed by alkylating the hydroxyl substituents within the silk fibroin to form a carboxylic acid-modified silk. This may be performed by coupling a haloalkylcarboxylic acid (e.g., $ClCH_2COOH$) under basic conditions to form the carboxylic-modified silk.

In some embodiments, the linking agent is further formed by contacting the carboxylic-modified silk with a diazonium salt comprising one or more of the aforementioned chemical moieties. The reaction couples the chemical moiety to the carboxylic acid. As used herein, the term "diazonium salt" may refer to a group of organic compounds with a structure of $R-N_2^+ X^-$, wherein R can be any organic residue (e.g., the one or more aforementioned chemical moieties) and X is an inorganic or organic anion (e.g., halogen). A diazonium salt can be formed by the treatment of aromatic amines (e.g., aniline) with sodium nitrite in the presence of a mineral acid and methods for synthesizing diazonium salts are known to those of skill in the art. See for example WO 2006/014549, WO 2004/108633 and WO 2001/025341, which are incorporated herein by reference.

In some embodiments, the method further includes coupling the haloalkyl substituent to the linking agent to form the modified silk. In some embodiments, coupling the haloalkyl substituent to the linking agent includes contacting a halonium salt with the linking agent. As used herein, a "halonium salt" may refer to a group of organic compounds with a structure of $(R_1)(R_2^+)(R_3) R_4^-$, where $R_1$ is the haloalkyl substituent; $R_2^+$ is a halo substituent selected from the group consisting of fluoro, chloro, bromo, and iodo; $R_3$ is any organic residue (e.g., an aryl group, a cyclic alkyl substituent, a $C_1$-$C_{10}$ linear or branched alkyl substituent, or hydrogen); and $R_4$ is an inorganic or organic anion (e.g., $^-N(SO_2CF_3)_2$). FIGS. 1-3 illustrate a non-limiting example of forming a modified silk in accordance with the present disclosure.

In some cases, the method includes forming a solid form of a silk fibroin material prior to addition of the one or more haloalkyl substituents. In these cases, the one or more haloalkyl substituents can be heterogeneously distributed within the solid form and will be more highly concentrated at the surface of the solid form. In some cases, the solid form can be made by a thermal molding process.

In the case of solid forms, the addition of the one or more haloalkyl substituents can reduce the water uptake of the solid form by at least 30% relative to an otherwise identical solid form that is lacking the one or more haloalkyl substituents and optionally any respective linking agents. One consequence of the reduced water uptake is that mechanical strength of the solid form is better maintained in aqueous environments when compared with silk fibroin solid forms lacking the one or more haloalkyl substituents.

The modified silk described anywhere herein can be a modified silk fibroin.

For clarity, features described in this section are combinable with features described in the preceding section, without limitation unless the context clearly dictates otherwise (e.g., a water contact angle is not combinable with an aqueous solution embodiment).

EXAMPLES

The following examples set forth, in detail, ways in which the compositions described herein may be synthesized, and will enable one of skill in the art to more readily understand the principles thereof. The following examples are presented by way of illustration and are not meant to be limiting in any way.

Example 1

An Exemplary Method for Tuning the Hydrophobicity of Silk Fibroin

Materials and Methods

Silk processing. Aqueous silk solutions were prepared according to previously published protocols with minor adjustments. See, e.g., Rockwood, D. N.; Preda, R. C.; Yucel, T.; Wang, X.; Lovett, M. L.; Kaplan, D. L., Materials fabrication from *Bombyx mori* silk fibroin. Nature protocols 2011, 6 (10), 1612-1631. All chemicals used for processing and modification as described in this section were supplied by Sigma-Aldrich unless otherwise noted. *Bombyx mori* cocoons (Tajima Shoji, Yokohama, Japan) were degummed by boiling 5 g in 1 L of 0.02 M sodium carbonate for 30 min to remove sericin. Insoluble silk fibroin fibers were pulled apart frequently to ensure uniform degumming. At the end of the 30-min degumming period, extracted silk fibroin (herein referred to as silk) was immersed in room-temperature deionized (DI) water (resistivity ≥18 MΩ). After rinsing several times under running DI water, the silk was placed on clean aluminum foil and dried in a fume hood at ambient temperature for at least 12 h. Dry silk was packed tightly into a dry beaker, and 9.3 M lithium bromide was added to establish a final concentration of silk of 20% w/v. The beaker was tightly covered with aluminum foil and heated in a 60° C. oven for 3-4 h, or until the solution was transparent. The solution was then transferred to 3.5 kDa molecular weight cut-off (MWCO) cellulose dialysis tubing (Spectra/Por), and dialyzed against DI water for three days. The resulting aqueous silk solution was transferred into 50 mL Falcon tubes and centrifuged for three 20-min cycles to remove insoluble impurities (~12,700 g, 4° C.). Resulting silk concentrations ranged from 6-7.5% w/v, and solutions were stored at 4° C. for up to three months.

After extraction, silk was further modified in two stages to enhance primary amine content for subsequent fluoroalkylation (FIG. 2, steps 1 and 2). First, carboxylic acid functionality was enhanced following published methods. See, e.g., Serban, M. A.; Kaplan, D. L., pH-Sensitive ionomeric particles obtained via chemical conjugation of silk with poly (amino acid) s. *Biomacromolecules* 2010, 11 (12), 3406-3412; and Burke, K. A.; Roberts, D. C.; Kaplan, D. L., Silk fibroin aqueous-based adhesives inspired by mussel adhesive proteins. *Biomacromolecules* 2015, 17 (1), 237-245. Briefly, aqueous silk solutions were diluted to 0.6% w/v, and pH was adjusted to 13 via addition of 10 M sodium hydroxide. Solid chloroacetic acid was added to the solution (final concentration=10 M) and gently stirred for 1 h to mediate carboxylic acid addition to serine and tyrosine residues on the silk backbone. Monobasic sodium phosphate was added as a buffer (4 mg/mL), and the solution was neutralized with 10 M hydrochloric acid. The solution was stirred for 30 min, followed by dialysis against DI water for 3 days (MWCO=3.5 kDa). The solution was flash-frozen in liquid nitrogen and lyophilized. The lyophilized product, referred to as carboxylic acid-modified silk, was tightly wrapped in parafilm and stored at −18° C. until further use. The $^{13}$C NMR spectra of native silk and carboxylic acid-modified silk in D20 are not illustrated. Two new peaks appear in the spectrum of the carboxylic-acid modified silk. The peak at ~175 ppm likely corresponds to the carboxylic acid residue covalently attached to the silk upon reaction with chloroacetic acid. The other peak, at ~45 ppm, likely corresponds to the $CH_2$ group present in chloroacetic acid. These results support the covalent attachment the carboxylic acid residue to the silk fibroin.

To prepare silk with the enhanced amine content required for subsequent processing, we utilized a synthetic strategy that has previously been reported to enrich primary amine content of enzymes (see, e.g., Rodrigues, R. C.; Barbosa, O.; Ortiz, C.; Berenguer-Murcia, Á.; Torres, R.; Fernandez-Lafuente, R., Amination of enzymes to improve biocatalyst performance: coupling genetic modification and physicochemical tools. *RSC Advances* 2014, 4 (72), 38350-38374), as well as biologically-derived and synthetic polymers (see, e.g., Nakajima, N.; Ikada, Y., Mechanism of amide formation by carbodiimide for bioconjugation in aqueous media. *Bioconjugate chemistry* 1995, 6 (1), 123-130; and Madison, S. A.; Carnali, J. O., PH optimization of amidation via carbodiimides. *Industrial & Engineering Chemistry Research* 2013, 52 (38), 13547-13555). First, lyophilized carboxylic acid-modified silk was dissolved in equal parts DI water and 0.1 M MES buffer (pH=4.7), to a final concentration of 35 mg/mL. Separately, a solution of identical volume was prepared by dissolving ethylene diamine dihydrochloride in 0.1 M MES buffer (concentration of ethylene diamine dihydrochloride=0.5 g/mL), and the pH was adjusted to ~5.5 using 1 M NaOH. A third solution containing 1-ethyl-3-(3-dimethylaminopropyl) carbodiimide (EDC) was prepared in 0.1 M MES buffer (400 mg/mL), and added to the carboxylic acid-modified silk solution (2.4 mL/g silk). The ethylene diamine dihydrochloride solution was added, and the pH was adjusted to 5.5. The reaction mixture was gently stirred for 18 h at room temperature to facilitate carbodiimide coupling. The solution was then dialyzed against DI water for 3 days (MWCO=3.5 kDa). Following dialysis, the pH of the modified silk solution was adjusted to 10.5-11 using 5 M NaOH to ensure that all primary amines were present as their free base. The free amine is required for subsequent processing. The solution was flash-frozen in liquid nitrogen and lyophilized. After lyophilization, the product was milled using a benchtop analytical mill (Cole-Parmer) to enhance sample uniformity. This product, referred to as amine-modified silk, was tightly wrapped in parafilm and stored at −18° C. until further use.

General Procedure for the Synthesis of Iodonium salts. Four iodonium salts with varying fluorocarbon chain length were prepared, given the abbreviations C2, C4, and C8 (FIG. 3). These Iodonium salts were prepared according to existing literature methods. See, e.g., Umemoto, T.; Gotoh, Y., Syntheses of (1,1-dihydroperfluoroalkyl)aryliodonium triflates and their analogues. *Journal of Fluorine Chemistry* 1985, 28 (2), 235-239; DesMarteau, D. D.; Montanari, V., Chem Commun 1998, (20), 2241-2242; and DesMarteau, D. D.; Lu, C., Syntheses and lipophilicity measurement of Na/N-terminus-1,1-dihydroperfluoroalkylated α-amino acids and small peptides. *Journal of Fluorine Chemistry* 2007, 128 (10), 1326-1334.

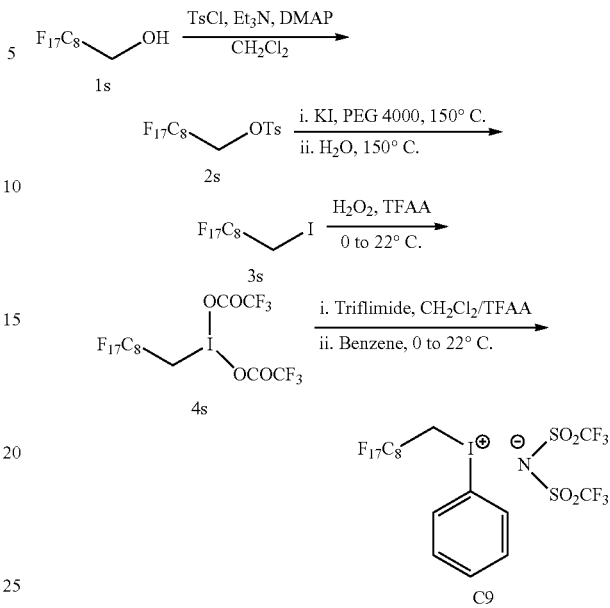

Scheme S1. Synthesis of C9 Iodonium Salt 1H,1H-perfluorononyl tosylate (2 s)

1H,1H-perfluorononan-1-ol (1s) was purchased from Synquest Labs as starting material for the synthesis of the C9 iodonium salt. Tosylation of the alcohol functionality was performed by dissolving 25 g (0.055 mmol) of starting material in $CH_2Cl_2$ (120 mL) along with p-toluenesulfonyl chloride (10.58 g, 1 eq.), triethylamine (11.24 mL, 1.44 eq.), and a catalytic amount of 4-dimethylaminopyridine (50 mg). The mixture was stirred at ambient temperature for 16 h, then extracted with 2×100 mL of 1 M HCl and 2×100 mL of $H_2O$. The organic layer was dried over $Na_2SO_4$ and then the solvent removed in vacuo to afford a white solid, 2s (31 g, 93% yield). $^1$H NMR (CD3CN, 500 MHz) δ 7.83 (d, J=9 Hz, 2H-Ar), 7.47 (d, J=9 Hz, 2H-Ar), 4.57 (t, J=15 Hz, 2H), 2.45 (s, 3H).

1H,1H-perfluorononyl iodide (3s)

Compound 2s (31.02 g), PEG 4000 (75 g), potassium iodide (17.27 g, 2 eq.) were mixed in a 500 mL round-bottom flask. The solid mixture was liquefied by heating to 150° C. and stirred for 7.5 h, then allowed to cool to <100° C., at which time $H_2O$ (200 mL) was added. A 25 mL Dean-Stark trap was set up and the temperature was raised back to 150° C. to collect the product by steam distillation. The white solid product can be used in the next step after separation from the distilled water. Yield: 18 g, 0.032 mol, 63%; $^1$H NMR (CD3CN, 500 MHz) δ 3.79 (t, J=19 Hz, 2H).

(Bis-trifluoroacetoxy)iodo-1H,1H-perfluorononane (4s)

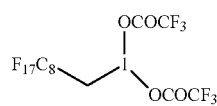

Oxidation of the iodide 3s (17.66 g) to form the iodoso compound 4s was performed with trifluoroperacetic acid in cold trifluoroacetic anhydride. Trifluoroacetic anhydride (56.7 mL, 12.9 eq.) was cooled in a −22° C. bath. After adequate cooling (~15 min), 30% w/w $H_2O_2$ (3.54 mL, 1.1 eq) was added dropwise. After 10 min the −22° C. bath was replaced with a 0° C. bath for 10 min. At this point, a condenser (no water) was attached, and the solution then stirred in the dark for 22 h. The volatiles were removed in vacuo and the white solid product used without further purification. Yield: 22 g, 0.028 mol, 88%; $^1$H NMR (CD3CN, 500 MHz) δ 5.22 (t, J=17 Hz, 2H).

1H,1H-perfluorononyl) phenyliodonium N,N-bis(trifluoromethyl-sulfonyl)imide (C9)

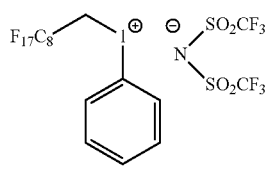

Compound 4s (22 g) was subjected to a Friedel Crafts type reaction to afford the final salt. Solid 4s was suspended in $CH_2Cl_2$ (35 mL) together with 8.64 grams (1.1 eq.) of trifluoromethanesulfonimide 5, and 3 mL of TFAA. This mixture was left to stir for 30 min, resulting in a solution, and then cooled in a 0° C. bath for 10 min. Benzene (1.2 eq.) was added rapidly with a Pasteur pipette and the reaction was capped with a Teflon-wrapped glass stopper and left to stir for 1 h. After this time, the ice bath was removed, and the reaction continued for 18 h in the dark under N2. This solution was then concentrated to an oil and placed under high vacuum for ~4 h. This was followed by addition of ice to promote crystallization. After crystals were visible, more ice and water were added and the mixture was stirred for 25 min, then filtered using a glass frit. The solid was washed several times with 5 M $NaHCO_3$ until the washings had a neutral or slightly basic pH (pH-8). The solid was then collected and lyophilized. (Note: if crystals do not form, a $H_2O$ and $CH_2Cl_2$ extraction may be performed, in this case the organic layer should be collected and dried over $Na_2SO_4$, taken to dryness, and the product recrystallized in ice). After crystals were collected and adequately dried, they were dissolved in $CH_2Cl_2$ using gentle heat and sonication. Once proper dissolution was achieved, the mixture was placed in a −20° C. freezer for 12 h to recrystallize. The contents of the flask were then poured over a glass frit and the solids were collected and dried under high vacuum, affording C9 as a beige solid, (19 g, 74% yield). $^1$H NMR (CD3CN, 500 MHz) 4.88 (t, J=18 Hz, 2H), 7.64 (t, J=8 Hz, 2H), 7.85 (t, J=8 Hz, 1H), 8.18 (d, J=8 Hz, 2H). $^{19}$F NMR (CD3CN, 470 MHz) −80.3 (s, 6F), −81.5 (t, 3F), −104.4 (quint, 2F), −121.7 (m, 4F), −122.2 (m, 4F), −123.2 (m, 2F), −126.6 (m, 2F). Positive mode ESI-MS 637.03 (cf. iodonium cation m/z=637.098).

Ninhydrin quantification. A standard ninhydrin quantification was performed to quantify free amine in the fluorinated silks, as well as the carboxylic-acid modified and amine-modified silk control; this assay was adapted from literature methods. See, Friedman, M., Chemically Reactive and Unreactive Lysine as an Index of Browning. 1982, 31 (Supplement 3), 5-14. A ninhydrin solution was prepared by dissolving 2 g ninhydrin and 0.3 g hydrindantin in N2-saturated DMSO in a dark glass container. A 4 M lithium acetate buffer was made by dissolving 16.8 g LiOH in 40 mL of $H_2O$ with subsequent addition of 30 mL of glacial acetic acid. This buffer solution was stirred and the pH was adjusted to 5.2. To the ninhydrin solution, 25 mL of the lithium acetate buffer were added. A calibration curve was constructed using a 3.05 mM stock solution of leucine in $H_2O$. 0.5 mL of the 1.5-fold serially diluted solutions were added to a 2 mL Eppendorf tubes. To these vessels 0.42 mL of the ninhydrin solution was added and the Eppendorf tubes were vortexed, covered in foil, and placed in a heating block at 100° C. for 15 min. The samples were cooled in an ice bath for ~2 min. To each sample, 1 mL of 50% EtOH/$H_2O$ was added and mixed by Vortex. Calibration samples were plated in a 96-well plate and the absorbance at 570 nm was read using a Thermo Scientific Varioskan Lux plate scanner and analyzed with Skanit RE 4.1 Software. To assess free amine content in modified silk samples, 5 mg of each sample were dissolved in 0.5 mL $H_2O$ and the above procedure was repeated. The calibration curve and linear regression used to analyze samples in the ninhydrin assay are not shown. The calibration curve shows a linear relationship between primary amine concentration and absorbance over the relevant concentration range for this study.

Film casting. Modified silk compounds were dissolved in 1,1,1,3,3,3-hexafluoro-2-propanol (HFIP, ≥99%) at concentrations of 5% w/w, except for C4 silks which were dissolved at a concentration of 2.5% w/w due to solubility constraints. All work with HFIP was performed in a fume hood. Silk solutions were freshly prepared in glass scintillation vials and were wrapped in parafilm before heating for ~30 min in a 60° C. water bath to facilitate dissolution. Films were fabricated by drop casting solutions on to clean glass cover slips (50 µL per $cm^2$), which were then dried in a fume hood for a minimum of 6 h. All films were analyzed <72 h after drying.

Seven unique films were prepared for analysis: three controls (silk-only, carboxylic-acid modified silk, amine-modified silk) and four fluorocarbon silks (C2, C4, C8, and C9). Fluorocarbon silks were abbreviated based on the iodonium salt used to prepare the silk.

Contact angle measurement. The wettability of fluorinated silk films and controls was assessed using two different contact angle goniometers (ramé-hart 250-F and 200-F1). A 2-7 µL drop of ultrapure water was placed on the film surface, and the resulting drop profile was fit using the on-board DROPimage Advanced software. The static water contact angle (WCA) was determined from the profile fits.

Statistical analysis. Quantitative ninhydrin and WCA data are presented as the mean one standard deviation. A minimum of three technical replicates were analyzed on a minimum of three separate samples (N=9) unless otherwise noted. One-way analysis of variance tests (ANOVA, significance level=0.05) with Tukey post hoc tests were run for data from the ninhydrin assay, as well as for WCA values collected on modified and control silk films. XPS compositions are reported as single data points, or averages±95% confidence interval.

Composition analysis by X-Ray photoelectron spectroscopy (XPS). XPS was used to measure differences in surface chemical composition and chemical binding environments of fluorinated silk films and control silk films (Thermo Scientific K-Alpha+ XPS system). Samples were placed in a vacuum desiccator for at least 24 h prior to analysis, and transported to the instrument under vacuum to minimize contamination. Samples were affixed to the XPS sample holder using copper clips, which also established electrical contact with the instrument. X-rays were generated using a monochromated aluminum Kα source (energy=1.4866 keV, line width=0.85 eV). An X-ray spot size of 400 m was utilized for all data collection, and an ultra-low energy electron flood gun was employed for charge compensation. To identify elements on the surface, high-resolution scans (pass energy=50 eV, step size=0.05 eV, 5 scans/sample) were collected in the following order: F1s, C1s, S2p, N1s, O1s, Si2p, a full spectrum survey, F KLL (an Auger peak, to confirm the presence of fluorine), Na1s, and Cl2p. Survey spectra (0 to 1350 eV binding energy, 200 eV pass energy, 1.0 eV step size, 5 scans/sample) were collected to check for impurities and to verify element scans. High-resolution spectra were used for composition analysis.

Data analysis was performed using CasaXPS version 2.3.18. Unless otherwise noted, all element spectra showing a peak above background noise were fit using a Shirley background, and 30% Lorentzian/70% Gaussian peak shapes with full width at half maximum values constrained to the range 0.4 to 2 eV. The signal intensity at the endpoints of the fitting region were defined as an average of 21 data points (10 data points to either side of the selected endpoint), unless otherwise noted. For peaks that exhibited spin-orbit splitting, ThermoFisher Avantage software values were used to fix the peak separation energy (Cl2p, 1.6 eV; S2p, 1.16 eV; and Si2p, 0.63 eV) and Scofield values (calculated photoionization cross-sections—see, e.g., Scofield, J., Hartree-Slater Subshell Photoionization Cross-Sections at 1254 and 1487 eV. *Journal of Electron Spectroscopy and Related Phenomena* 1976, 8 (2), 129-137) were used to determine the expected peak ratio. Standard relative sensitivity factors provided by ThermoFisher were used for all element quantification.

The spectra were referenced to the N1s peak of a close chemical analogue: the N1s binding energy of the amide group in nylon-6,6 at 399.81 eV (Beamson, G.; Briggs, D. J., *High resolution XPS of organic polymers: the Scienta ESCA300 database*. John Wiley: Chichester, 1992, p. 196). A similar amide N1s peak is expected to be present in virtually every amino acid in silk, and largely unaltered between the fluorinated and non-fluorinated silks considered. Signals from the primary and secondary amine groups, which arise during functionalization and have a slightly different binding energy, are expected to be overwhelmed by the signal from the more abundant amide groups.

Four elements required adjustments to the fitting method described above: C, F, N, and O. In the case of C1s, three peaks were used for the set of peaks at the lower end of the binding energy ("main") range (ca. 281 to 291 eV). For native, amine-modified, and C2 silk, one peak was used to fit the $CF_x$ region (between ca. 291 to 295 eV), and the $CF_x$ and main peak regions were fit to separate backgrounds. C4, C8, and C9 silk were fit with a single background, because the $CF_x$ and main peaks overlapped too much to be separated. For these spectra, two peaks were fit to the $CF_x$ region. The background endpoints of the C2 and native silk $CF_x$ region were set to an average of a 7 data point window, centered on the chosen endpoint. This narrower range was necessary to avoid including peak shoulders in the background endpoint average. $CF_2$ and $CF_3$ groups are placed at ca. 292 eV and 294 eV, respectively, by ThermoFisher's reference software. A closer examination of the literature, including polymer reference databases, shows that binding energies of these two functional groups are spread throughout this range, varying with bonding environment. The $CF_2$ and $CF_3$ groups resulting from the fluorinated chain are expected to overlap with those of any residual HFIP and triflimide (discussed below); hence, XPS cannot reliably distinguish these peaks or permit unambiguous quantification of only the fluorinated chain contributions in these samples.

High-resolution C1s XPS spectra were fitted with up to five peaks to model binding environments present on the surface of the fluorinated and control silk films (data not shown). The amine-modified silk (panel b) shows predominantly aliphatic (binding energy ~285.0 eV), C—O/C—N (binding energy ~286.5 eV), and C═O-type (binding energy ~288.5 eV) signals. These binding environments are reasonable based on the unmodified silk spectrum (panel b). The C2 silk (panel c) displays these three binding environments, as well as a minor contribution for a higher binding energy environment (binding energy ~293 eV) that likely corresponds to $CF_3$ groups from triflimide, HFIP, and fluorinated alkyl chains. The C1s spectra of all other fluorinated silks-C4, C8, and C9—display a binding environment likely corresponding to a mixture of $CF_2$ and $CF_3$ functionality, again from triflimide, HFIP, and fluorinated chains. The $CF_x$ regions were fitted with two peaks at ca. 291.4-291.7 and ca. 293.2-293.7 eV, but for reasons described above, $CF_2/CF_3$ ratios cannot be reliably determined.

The deviation of elements' different matrix environments from the standards used to derive sensitivity factors presents a further challenge to accurate composition quantification. XPS sensitivity factors are typically determined by the manufacturer, which measures a known, standard material containing the element of choice. The true sensitivity factor of an XPS peak varies with bonding environment and especially matrix effects, and hence can be significantly different from default calibration factors. As is standard practice in the literature, we have chosen to use instrument calibration factors provided by ThermoFisher; measuring accurate calibration factors specific for the samples in question would require an additional set of composition measurements by a complementary technique—preferably with some additional samples to provide a calibration curve—and would therefore be dramatically more ambitious in scope than this study. However, sensitivity factor variation may explain some discrepancies in our data. In particular, the fluorine at. % shown in Table 2 is significantly larger than the amount predicted by the $CF_x$ signal. Explanations that exclude a difference in C1s C—C, C1s C—F, and F1s sensitivity factors require that: a) ca. 10 at. % F exists in these materials outside organofluorine compounds (e.g., as a metal fluoride) and/or b) all $CF_x$ area is due to $CF_3$. Both explanations are unlikely, suggesting that some of the composition discrepancy between the F1s and C1s $CF_x$ signals may be due to sensitivity factor mismatch.

Figure 7:
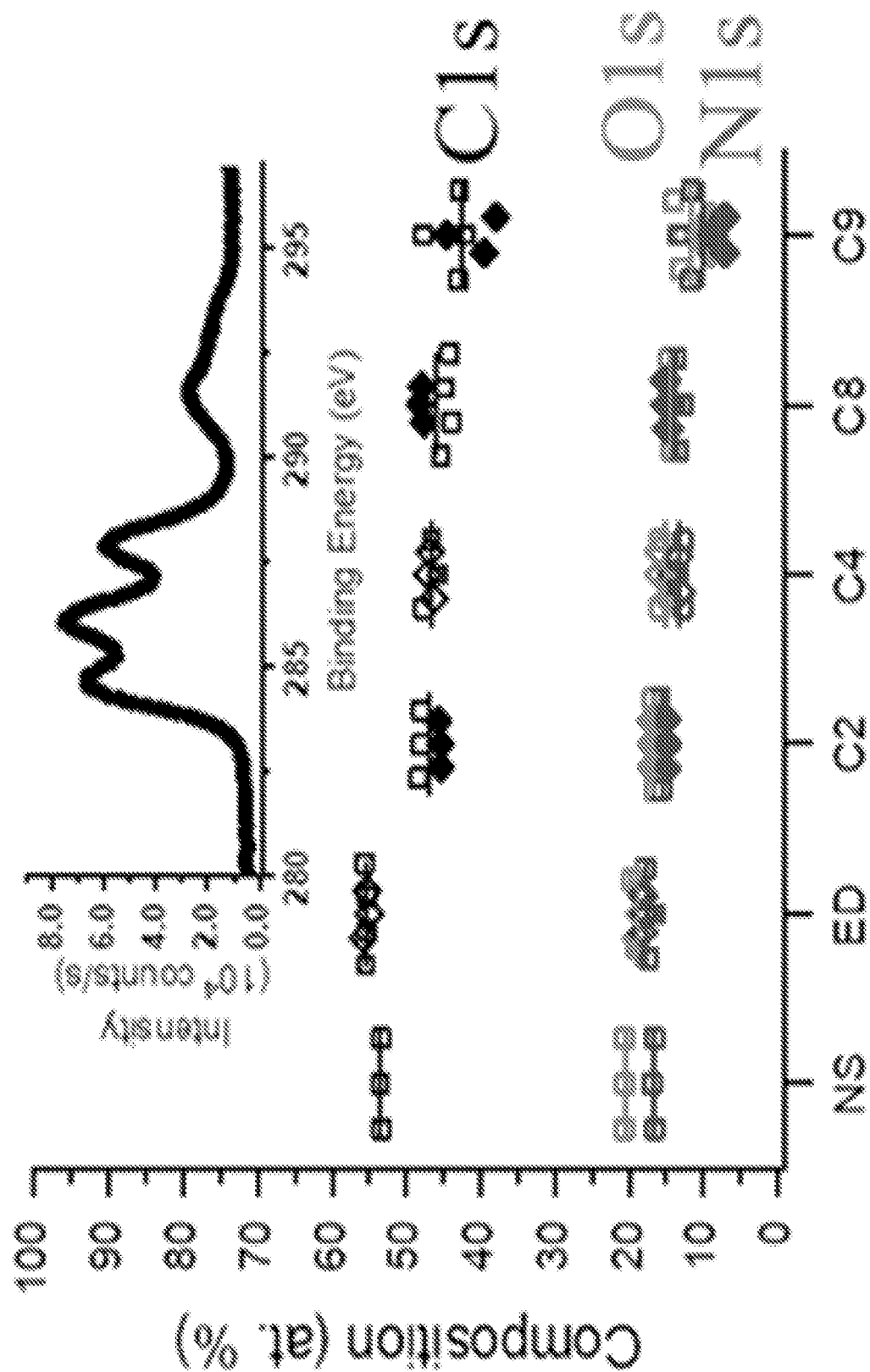
FIG. 7 shows atomic composition of sampled films determined by high-resolution XPS for carbon, oxygen, nitrogen.

Fluorine peaks for native, amine-modified, C2, and C4 silk were fit with a single peak with a Lorentzian/Gaussian ratio of 0.4922. Some variation in L/G ratio is expected across elements and bonding environments. By adjusting the L/G value, we better capture the broad tails of the F 1s peak. This specific value was selected by fitting 4 analysis spots on one cast sample per silk type (3 in the case of C2 silk), allowing the L/G ratio to vary as a fitting parameter, and then averaging all of these L/G values. In FIG. 7, these casts are indicated with square symbols. Fits with the new, averaged L/G ratio were then applied to all samples. For C8 and C9, the peak shape and area were best captured by two peaks of L/G 0.4922. The smaller peak at low binding energy is consistent with ThermoFisher reference values for metal fluoride, and is not likely part of the fluorinated chain. For all test spots considered, this low binding energy peak consists of at most 0.8 at. % fluorine for C8 and 1.3 at. % for C9. The detection limit of this peak was estimated to be 0.3 at. %, by fitting two peaks to an F1s spectrum where the presence of this peak is ambiguous. To estimate the area not captured by these standardized fitting procedures (fixed L/G 0.4922, with either one or two peaks), the data were smoothed with a quadratic Savitzky-Golay smoothing function with a 5 data point window and integrated with the same background and range as the original fit. Compared to the fitted peaks, the smoothed fits captured additional area equivalent to less than or equal to ca. 0.1 at. % for native silk, amine-modified silk, and C8 silk and 0.2 at. % for C2, C4, and C9 silk. The error of individual F 1s fits is estimated to be at least equivalent to these values, and at most equal to ca. 0.3 at. %, the detection limit of the smaller peak at higher binding energy.

The main oxygen peak was best fit with two peaks, rather than one. Due to significant overlap of these peaks, it was not possible to establish a unique fit that unambiguously identifies the oxygen bonding in the modified silk. To accommodate these peaks and nearby satellite peaks (discussed below), it was necessary to adjust the endpoints of the background to an average of 1 data point surrounding the chosen end point location. The exceptions were the C4 and C2 fits, which used a window of 21 data points (10 to either side of the end point) for the main peaks, and a window of 7 data points for the satellite peak background endpoints. To bound the possible fits, and to bring some consistency to fits from sample to sample and spot to spot, the peak separation was fixed to 1.25 eV. The value is the estimated energy separation between O1s peaks corresponding to the OH group in serine or ether group in the fluorinated chain, and the C=O groups in the silk backbone. Reference binding energy values for these peaks were the ether group in polytetramethylene glycol (532.62 eV, referenced to C—C at 285 eV; Beamson and Briggs p. 88) and the C=O group of nylon 6,6 (531.37 eV, referenced to C—C at 285 eV; Beamson and Briggs p. 196). The OH groups present in serine in native silk might be better represented by the OH group in poly(vinyl alcohol) (532.74 eV, ref. to C—C at 285 eV; Beamson and Briggs p. 96), 0.13 eV higher in binding energy. For simplicity, a single peak separation value was used; the ether value was selected because the alcohol groups should generally have been converted during processing to ether linkages (except in native silk). Constraining the peak fitting to enforce this 1.25 eV separation resulted in relatively consistent peak ratios of ether to C=O for each type of silk and peak positions of ca. 532.6-532.8 eV and 531.4-531.6 eV, for the ether group and C=O, respectively. Any residual bistriflimide or HFIP entrained in the film would also contain oxygen, and are likely to contribute to the area of the higher binding energy peak.

Small, broad peaks on the high binding energy side of the O1s region were also observed. These are thought to be O1s satellite peaks and were not included in total oxygen counts. Unless otherwise noted, the area (and potential contribution) of these peaks were estimated by fitting a separate background region with 1-3 peaks. It was not possible to fit two background regions to the O1s spectra of the second casting of C9 silk (three measurement spots), so separate peaks were fit alongside the main peaks, and then omitted from quantification. If quantified as oxygen, the maximum contribution of these high binding energy peaks are less than 0.3 at. % for C2 and C4, 0.4 at. % for native, amine-modified, and C8, and less than 0.6 at. % for C9 silk. As with fluorine, the spectra were smoothed and integrated to estimate the area not captured by the fitting procedure. The compositions determined by this procedure had ca. 0.2 at. % or less additional oxygen composition than the original fits. The exception was the smoothed and integrated composition of the second cast of C9, which had ca. 0.6 at. % or less additional oxygen. The potential underestimation of peak area was due to the necessity of fitting only one background region—this caused an underestimate of the satellite region background, leading to a lower computed area for the original fitting scheme. Ultimately, these quantities are small relative to the amount of oxygen present, and hence not a major concern for quantification. The error of individual O1s fits is estimated to be at most equal to the difference between the fitted peaks and the smoothed, integrated peak area, described above.

Nitrogen peaks for native and amine-modified silk were fit with a single peak, while C2, C4, C8, and C9 were fit with two peaks, all with a Lorentzian/Gaussian ratio of 0.7236. This value is the average of the L/G value of 4 spots on one cast sample per silk type (3 in the case of C2 silk) resulting when the peaks were fit with the L/G ratio allowed to vary as a fitting parameter. In FIG. 7, these casts are indicated with square symbols. As with F 1s, adjusting the L/G value better captured the broad tails of the N1s peak. The smaller peak at high binding energy (ca. 402.5 eV) is small relative to the total nitrogen composition. It was included in nitrogen quantification because there were no compelling reasons to exclude it (for example, evidence of a nitrogen-containing contaminant matching that binding energy). For all test spots considered, this low binding energy peak corresponds to at most 0.4 at. % nitrogen for C2, 0.3 at. % for C4, C8, and 0.2 at. % for C9. The detection limit of this peak was estimated to be 0.2 at. %, by fitting two peaks to an N1s spectrum where the presence of this peak is ambiguous. As described for fluorine and oxygen, the data were smoothed and integrated to estimate the area not captured by the fit. Compared to the fitted peaks, the smoothed fits captured additional area equivalent to less than or equal to ca. 0.1 at. % for native silk, C2, C4, C8, and C9 silk and 0.3 at. % for amine-modified silk. The error of individual N1s fits is estimated to be at least equivalent to these values, or to ca. 0.2 at. % (the peak detection limit), whichever is greater.

Impurities detected by XPS were sodium and chlorine (typical residues in silk preparation), sulfur (likely from the triflimide anion of the iodonium salt), and silicon (Table 1). Silicon is detectable only in the native, amine-modified, and C9 silks, likely due to areas of exposed glass substrate or very thin (<10 nm) silk films, which permit photoelectrons from the substrate to reach the detector. In addition, fluorine was detected in the native silk and amine-modified silk. We believe this fluorine arises from residual casting solvent, HFIP, incorporated into the films.

The amount of fluorine-containing impurities can be estimated, to allow a more accurate assessment of the amount of fluorocarbon grafted to the silk by the iodonium salt treatment. Using the sulfur composition shown in Table 1 and assuming a 3:1 F to S ratio for residual triflimide salt, the triflimide contribution is estimated to be below 9 at. % for the fluorinated silk samples, and negligible for the native and amine-modified silk. Note that this triflimide residue must bear two oxygens for every sulfur, likely contributing to the portion of the O1s signal at higher binding energy. If it were present, the iodonium cation could also contribute fluorine; however, negligible iodine was detected in the survey scans. The highest concentration was ca. 0.06 at. %, easily detectable due to iodine's high sensitivity factor. At most, the associated fluorine contribution would be ca. 0.1 at. %, near the noise threshold of the instrument. Even if the iodine were underestimated by a factor of ten (e.g., owing to the low resolution of the survey scan), the associated fluorine contribution would be ca. 1 at. %; we believe the true value to be much less than this number.

The fluorine content due to HFIP is more challenging to estimate: the presence of fluorine on the surface of native and amine-modified silk is very likely due to HFIP, the only fluorine source these samples were exposed to. The amount of fluorine in these samples-6.6±0.5 at. % and 3.1±0.8 at. %, respectively-then provides an estimate of how much HFIP might be retained by the fluorinated silk films. Because the fluorinated samples are expected to be "omniphobic", we treat the amount of HFP found in the amine-modified silk (synthetically, the closest non-fluorinated analogue to the fluorinated silks) as an upper bound on the expected contribution of HFIP to the fluorine signal in the fluorinated silks. Because HFIP incorporates oxygen (as ROH) in addition to six fluorines, if the HFIP were contributing a substantially larger amount of the fluorine signal, a significant increase in the O1s signal would also have to appear. It does not; the total at. % O decreases with increasing degree of fluorination, and the fraction of the O1s signal observed at higher binding energy (closer to 533 eV, where the alcohol should contribute) stays near 30% for most samples, excepting amine-modified silk (13%) and C8 silk (44%). For the purposes of illustrating the sources of fluorine, we estimate fluorine contributions from HFIP as equivalent to the amine-modified silk (ca. 3 at. %) in the fluorinated silk samples, although we cannot definitively rule out this number being closer either to 0 at. % or to the native silk value of 6.6 at. %.

Impact of X-ray exposure on XPS composition. To explore the extent to which film composition changes with X-ray exposure from scanning, the following scans were performed on native and C9 silk films (casts are equivalent to square symbols in FIG. 7): ten sequential repetitions of a scan set consisting of single-scan passes of F1s, C1s, S2p, N1s, O1s, performed on "location 1" for each film. The films were then left pumping down in the instrument for 7.8 hours for native silk and 8.5 hours for C9, at which point these tests were repeated at the same location, and then in a new location ("location 2") for each film (8 hours later for native silk, and 8.8 hours later for C9 silk). For C9 silk, the initial scans of location 1 show the fluorine signal decreasing with each successive scan (23% area reduction from first to last scan). The C1s signal decreases in the C—$F_x$ region (ca. −23%), and increases in the region between 284 and 290 eV, especially in the peaks corresponding to C—C and C—O/C—N bonds (ca. +13% area). A very slight decrease was observed for S2p, and no significant change was noted for N1s. After 8.5 hours, these changes in the C1s and F1s scans had become more pronounced, that is, the first scans of this set had lower intensity than the last scans of the previous set. In addition, a small intensity change was observed as exposure time increased (ca. +3% for main C peaks, −18% for $CF_x$, and −13% for F1s; all relative to the first scan of this set). The peaks detected in location 2 and delayed location 1 scans on the C9 silk sample have similar shape and intensity, and the location 2 scans show a similarly small change in intensity with exposure time (ca. +4% for main C peaks, −8% for $CF_x$, and ca. −13% for F1s). The small peak on the low binding energy side of the F1s peak grew in location 1, staying at ca. 7-10% the size of the main peak during the first scan set, and reaching 18% by the end of the final scan set. An equivalent peak in location 2 remained between 8 and 10% of the size of the main F1s peak.

Location 1 on the native silk sample shows a much smaller reduction in fluorine and $CF_x$ area as a function of X-ray exposure. We observe a ca. 14% reduction in the F1s peak, mostly taking place during the initial scan set. Location 2 and a third location (measured ca. 15 minutes after location 2, only for native silk) both showed a similar

TABLE 1

| Element | NS Avg. (at. %) | NS 95% CI (at. %) | ED Avg. (at. %) | ED 95% CI (at. %) | C2 Avg. (at. %) | C2 95% CI (at. %) | C4 Avg. (at. %) | C4 95% CI (at. %) | C8 Avg. (at. %) | C8 95% CI (at. %) | C9 Avg. (at. %) | C9 95% CI (at. %) |
|---|---|---|---|---|---|---|---|---|---|---|---|---|
| C | 53.5 | 0.2 | 55.3 | 0.3 | 46.8 | 1.5 | 46.7 | 0.9 | 46.0 | 1.7 | 43 | 3 |
| Cl | 0.073 | 0.014 | 1.5 | 0.3 | 0.08 | 0.09 | — | — | 0.48 | 0.08 | 0.05 | 0.07 |
| F | 6.6 | 0.5 | 3.1 | 0.8 | 17.8 | 1.4 | 23 | 2 | 22 | 3 | 33 | 7 |
| N | 16.7 | 0.5 | 17.7 | 0.6 | 15.3 | 0.4 | 13.3 | 0.8 | 14.0 | 0.9 | 10 | 2 |
| Na | 1.34 | 0.08 | 2.1 | 0.3 | 0.71 | 0.03 | 0.38 | 0.14 | 1.07 | 0.13 | 0.90 | 0.08 |
| O | 20.61 | 0.14 | 18.9 | 0.4 | 16.8 | 0.2 | 15.2 | 1.0 | 14.6 | 0.6 | 11.7 | 1.9 |
| S | 0.13 | 0.03 | 0.11 | 0.03 | 2.5 | 0.4 | 1.5 | 0.3 | 1.5 | 0.3 | 1.36 | 0.17 |
| Si | 1.04 | 0.18 | 1.2 | 0.8 | — | — | — | — | — | — | 0.13 | 0.15 | reduction trend of ca. 10%, from first scan to last scan within each set. A small peak on the low binding energy side emerged in all locations (ca. 7-16% the area of the main peak). The main C1s peaks were essentially unchanged during the initial scans for location 1, 2, and 3.

Broadly speaking, the C9 samples showed a larger absolute change in peak area, consistent with the liberation or decomposition of carbon-bonded fluorine with X-ray exposure, and/or additional pump-down time removing volatile fluorinated compounds. The different behavior of native and C9 silk could be due to a difference in the included fluorine-containing compounds; the fluorine incorporated into the native silk is believed to be from HFIP, whereas the fluorine in C9 silk is likely a mixture of HFIP, bistriflimide, and covalently bound fluorocarbon. Teasing apart the relationship between fluorine composition, exposure time, spatial uniformity of composition, and pumping time would require a larger set of experiments that are beyond the scope of this study. Instead, we chose to note the presence of this signal decay, and to mitigate the issue to the greatest extent possible by minimizing total scan time, and scanning fluorine first, followed by carbon. This approach follows the standard treatment for fluorinated polymers potentially susceptible to damage induced by X-ray exposure.

Figure 4:
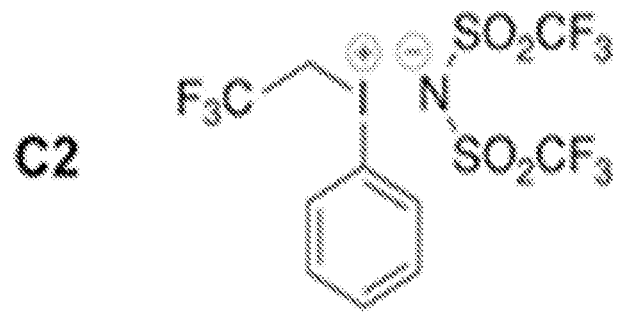
FIG. 4 shows the chemical structures of the trivalent iodonium salts that were used, denoted as C2, C4, C8, and C9 to represent the number of carbons in the chain.
Figure 4:
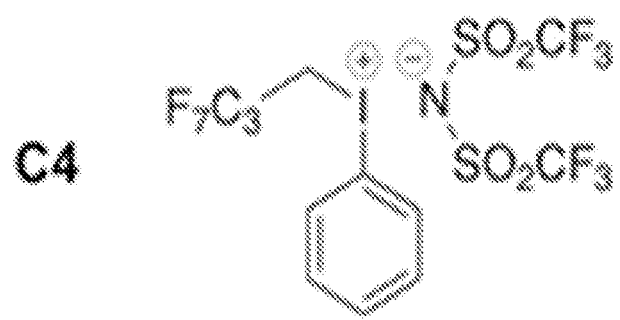
Figure 4:
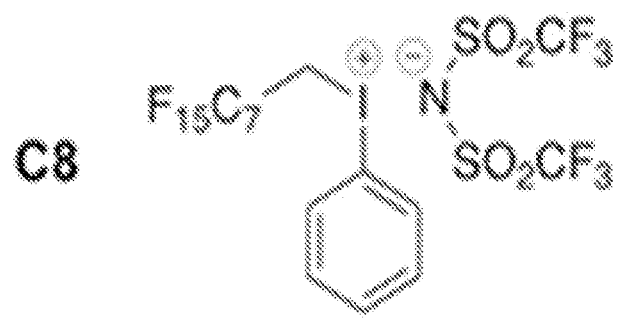
Figure 4:
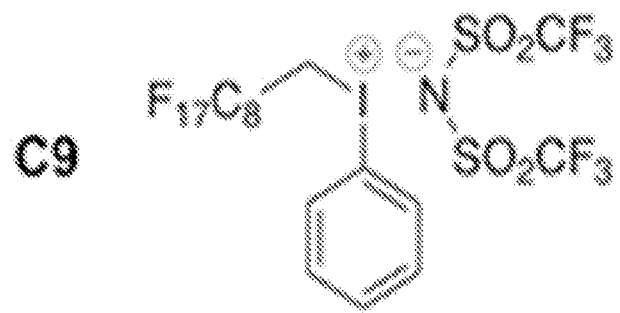
Figure 5:
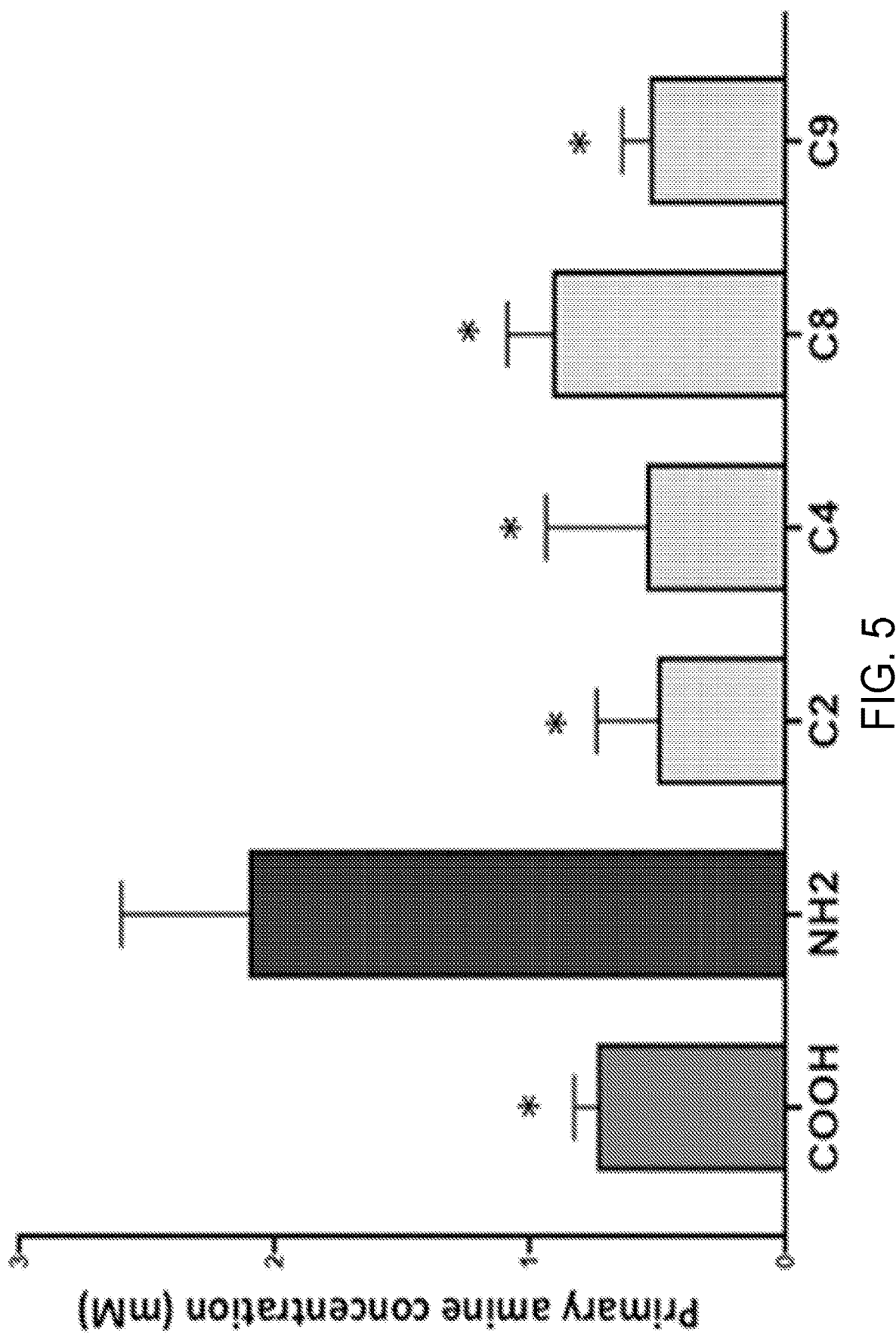
FIG. 5 is an example graph illustrating the average amine content for carboxyl-modified silk fibroin, amine-modified silk fibroin, and C2, C4, C8, C9 silk fibroin as measured via a ninhydrin assay. Significant differences from the amine-modified silk are indicated with asterisks *, determined by one-way ANOVA with Tukey post hoc test, $p<0.05$.

We report here a method wherein introducing fluorocarbon substituents enhances silk film hydrophobicity. Common methods to introduce fluorine-containing functionality onto proteins include N-terminal modification through reductive amination and introduction of unnatural amino acids and more. Here we adapt an approach originally designed for the purification of peptides prepared by solid-phase methods. In this approach, trivalent iodonium salts containing the desired fluorinated substituent react with a primary amine to form a new C—N bond; here, that new bond chemically grafts the fluorocarbon onto silk. However, silk side chains comprise only ~1 mol % primary amine, mostly from lysine and arginine. To overcome this limitation of the native silk, we have chemically modified hydroxyl-containing residues (20 mol %) to introduce primary amine functionality (FIG. 2). To demonstrate the tunability of this synthetic approach, we utilized four iodonium salt variants (C2, C4, C8, C9; FIG. 4) containing between 3 and 17 fluorine atoms. Introduction of these fluorocarbon groups, confirmed by X-ray photoelectron spectroscopy (XPS), increases the contact angle of water on the chemically modified silk films.

Figure 6:
FIG. 6 is a series of images illustrating the average contact angle values (±one standard deviation) and representative drop profile image for amine-modified silk, C2, C4, C8, and C9 silk.

The progress of the chemical modification of the silk was monitored using a ninhydrin test, a colorimetric assay specific for primary amines. Concentration data corresponding to primary amine content for the carboxylic acid-modified, amine-modified, and fluorine-modified silks are displayed in FIG. 6. First, a statistically significant enhancement in primary amine concentration is observed between the carboxyl-modified starting material and the amine-modified product. Second, after treatment with the iodonium salts C2-C9, all four fluorine-modified silks display a statistically significant decrease in primary amine content compared to the amine-modified silk. These results demonstrate that the diazonium coupling installs primary amines on the carboxyl-modified silk, and that these amines then react with the iodonium salts. We thereby infer the formation of covalent bonds between the fluorocarbon chains and the silk-bound amines. These fluorinated silks were used to drop-cast films for further analysis.

Water contact angle (WCA) goniometry was used to assess the wettability of fluorinated and control silk films. Data presented in FIG. 7 include WCA values, averaged over 3+ samples, and a representative drop shape image for each type of sample.

These WCA values demonstrate the tunability of this fluorination methodology. We observed WCA values ranging from 68±3° (for C2-silk) to 125±3° (for C9-silk). Notably, all WCA values for fluorinated silks are significantly greater than that of the amine-modified silk control (WCA=43±5°), or of native silk (WCA=60±2°). Remarkably, the C9-silk is more hydrophobic than Teflon (WCA=108°), despite most of the film simply being silk, with the surfaces decorated with fluorocarbon chains. The wide WCA range of >65o demonstrates the versatility of this silk surface modification technique.

In general, longer fluorocarbon chain lengths provide larger WCA values, although the values for C4 and C8 fall within error of each other. This similarity results in part from the relatively large error in the C4 data, which likely originates in morphological differences for C4-silk films. Specifically, after treating the amine-modified silk with the C4 iodonium salt, the resulting material had lower solubility in HFIP than the other fluorinated silks. Thus, a concentration of 2.5% w/v was used to cast C4-silk films (cf. 5% w/v for all other films). The C4 films exhibit a visibly rougher surface; this higher surface roughness may contribute to the relatively large WCA error.

To characterize the modified composition of the fluorinated silk films, high-resolution XPS analysis was performed on fluorinated and control silk films. To minimize the effect of X-ray induced damage to the fluorinated surface, fluorine and carbon high-resolution scans were performed before other elements. FIG. 7 displays the carbon, nitrogen, and oxygen contents for the different silk films, including the native silk (NS) and amine-modified silk (ED) controls. The relatively similar contributions observed from these three elements largely result from the silk protein. XPS samples were prepared by casting films for each sample type on two different days, in some cases using a different batch each day. Within a single film cast, indicated by the sample label and symbol shape, compositions measured at different locations on the film ranged from reproducible within instrument error (<1 at. %, e.g., C2) to highly variable (e.g., C9). The same is true of different casts of the same batch, and of the variation between batches.

Figure 8:
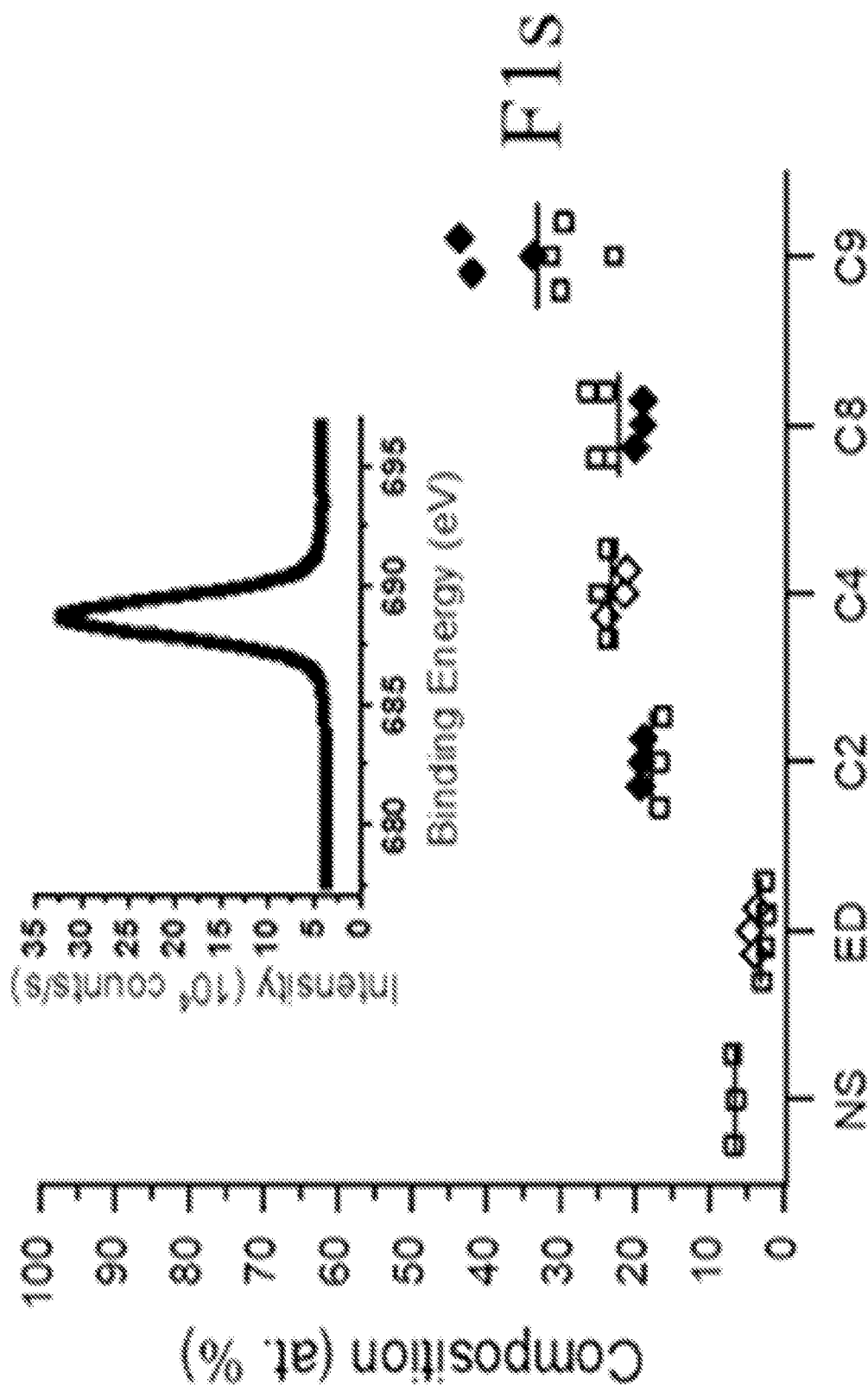
FIG. 8 shows atomic composition of sampled films determined by high-resolution XPS for fluorine (NS: native silk, ED: amine-modified silk), fluorine contributions include the fluoroalkyl chain in addition to triflimide salts and solvent (HFIP).

The inset in FIG. 7 shows a representative high-resolution C1s spectrum for a C9 silk film. We observe increasing contributions from higher binding energy (>290 eV) components as fluorocarbon chain length is increased, suggesting increased contributions from fluorine-bound carbon. FIG. 8 shows the fluorine composition for the modified and control silk films. Total fluorine content appears to increase as a function of fluorocarbon chain length for the fluorinated silk samples, with a maximum average observed at ca. 33 at. % for C9 (cf 66 at. % for Teflon). Further details of the XPS analysis and fitting procedures can be found in a journal article corresponding to the experiments shown in this Example from the inventors and their co-authors. A composition summary is shown in Table 2. CI=confidence interval.

Table 2

| Sample | Carbon at. % | 95% CI | Oxygen at. % | 95% CI | Fluorine at. % | 95% CI | Nitrogen at. % | 95% CI | Sulfur at. % | 95% CI | Other impurities at. % | 95% CI |
|---|---|---|---|---|---|---|---|---|---|---|---|---|
| NS | 53.5 | 0.2 | 20.6 | 0.2 | 6.6 | 0.5 | 16.7 | 0.5 | 0.13 | 0.03 | 2.45 | 0.19 |
| ED | 55.3 | 0.3 | 18.9 | 0.4 | 3.1 | 0.8 | 17.7 | 0.6 | 0.11 | 0.03 | 5.0 | 3.0 |
| C2 | 46.8 | 1.5 | 16.8 | 0.2 | 17.8 | 1.4 | 15.3 | 0.4 | 2.5 | 0.4 | 0.8 | 0.1 |
| C4 | 46.7 | 0.9 | 15.2 | 1.0 | 23 | 2 | 13.3 | 0.8 | 1.5 | 0.3 | 0.38 | 0.14 |
| C8 | 46.0 | 1.7 | 14.6 | 0.6 | 22 | 3 | 14.0 | 0.9 | 1.5 | 0.3 | 1.56 | 0.15 |
| C9 | 43.0 | 3.0 | 11.7 | 1.9 | 33 | 7 | 10.0 | 2.0 | 1.4 | 0.2 | 1.08 | 0.19 |

In addition to C, N, O, and F, we also detected other trace elements (<3 at. %) consistent with silk impurities, the glass substrate, and residual reagents from previous synthesis steps. A detailed treatment of these elemental composition data, in light of the synthetic procedure, suggests some adventitious fluorine could also be present in the film in three forms. First, the detection of sulfur in fluorinated silks suggests the presence of triflimide salts from the fluorinated silk synthesis, because the native silk backbone contains only a small amount of sulfur, consistent with the small sulfur content detected in the native and amine-modified silk samples. The triflimide contributions were estimated to be less than ca. 9 at. % F in fluorinated samples, and negligible in native and amine-modified silks. Second, a fluorine signal was observed in the native and amine-modified silk, suggesting contributions from some residual HFIP casting solvent (estimated to be ca. 3 at. % F in fluorinated silks). Third, an F1s peak appears in the metal fluoride region for C8- (<0.8 at. %) and C9-silk (<1.3 at. %). Estimates of these three contributions are discussed above.

Figure 9:
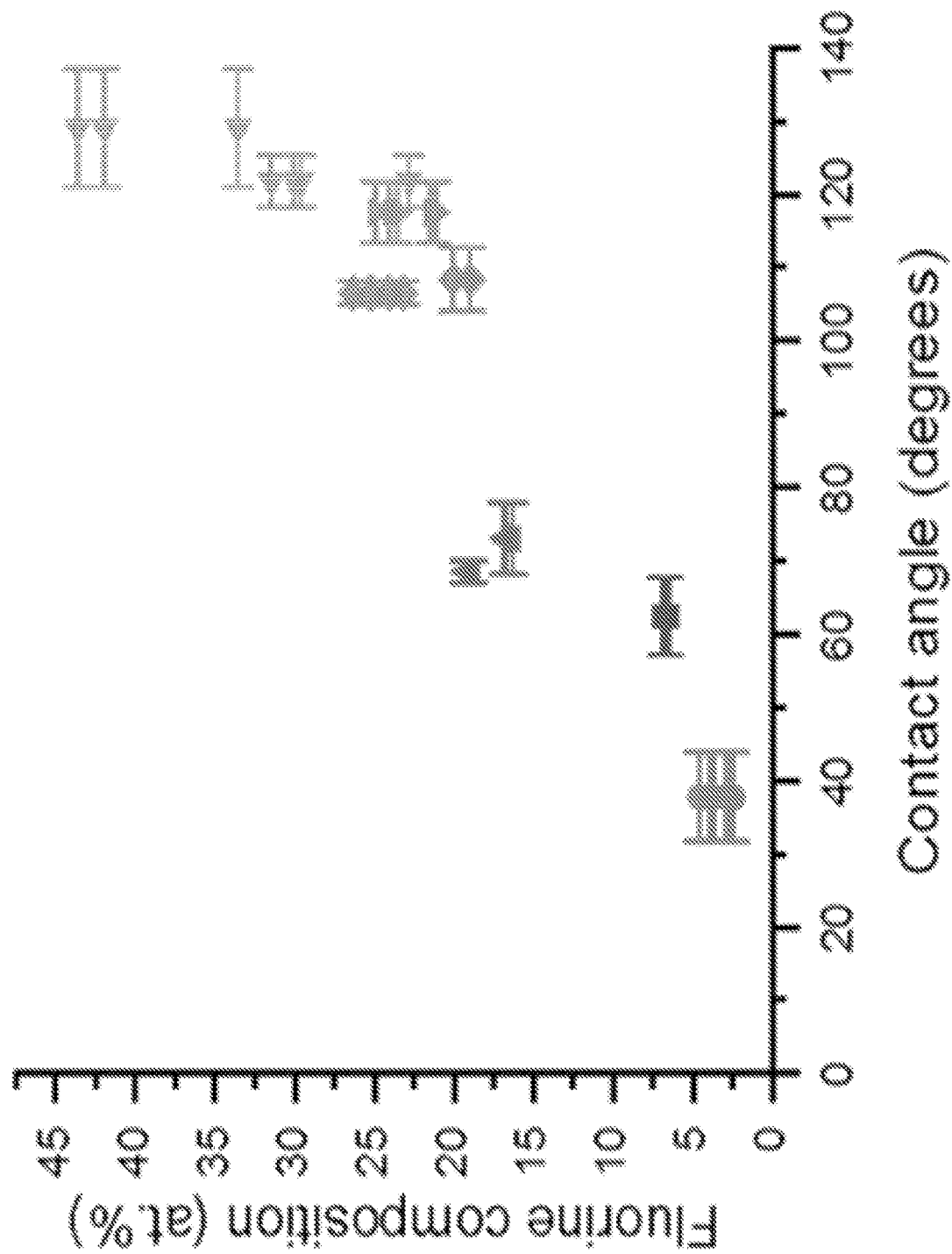
FIG. 9 show fluorine composition determined by XPS versus contact angle measured for native (square—■), amine-modified (circle—●), C2 (triangle with an apex pointing up—▲), C4 (triangle with an apex pointing down—▼), C8 (diamond—♦), and C9 silk (triangle with an apex pointing left—◄). Error bars are one standard deviation of at least 4 data points.

After correcting for these adventitious fluorine contributions, the trend of increasing fluorine content with increasing fluorinated chain length generally holds, though C4 and C8 have essentially the same fluorine content. This similarity in their corrected fluorine content may help explain the similar WCA values measured for these films. Collectively, the XPS data are consistent with silk modification via covalent bond formation between the amine residues on the silk and the fluorocarbon chain of the iodonium salt, albeit with the presence of some residual fluorinated compounds and other impurities from synthesis. Water contact angle and fluorine composition values are displayed together in FIG. 9. Despite some uncertainty in the composition analysis, this visualization highlights the relationship between hydrophobicity and chemical composition, and showcases the tunability afforded by this approach.

The overall motivation for this work was to fabricate a set of silk-based materials with tunable hydrophobicity. We found that this characteristic was controlled by the interplay of two variables: the amine content of the modified silk and the fluorine content of the iodonium salt. The amine concentration in the starting material plays an important role. Variability in the amine content of the amine-modified silk led to variability in measured WCA after fluorination. For example, two samples of amine-modified silk with average primary amine concentrations of 2.92 mM and 1.71 mM (determined via ninhydrin) were modified with the C9 iodonium salt, resulting in C9-silk films with WCA values of 125±2° and 116±2°, respectively (data not shown). We attribute this decrease of about 100 to a lower amount of fluorine on the silk surface due to the lower number of available amine sites for functionalization. As expected, we also observed that the hydrophobicity of the silk surface correlates strongly with the fluorine content of the silk.

We thus report a versatile synthetic method to append fluorocarbon moieties to silk fibroin. We have demonstrated the customizable nature of the surface chemistry and hydrophobicity of silk-based materials using this method, including by preparing silk samples more hydrophobic than Teflon. The solubility of these fluorinated materials in HFIP allows for a wide range of applications such as hydrophobic inks and coatings that may be useful in modulating the attachment of unwanted cells and other biological materials to implantable biomedical devices like stents and catheters.

Example 2

An Exemplary Method for Direct Heterogeneous Fluorination on Thermally-Molded Silk Constructs Regenerated amorphous silk fibroin nanoparticles (ASN) are prepared followed by methods described by Guo et al. (Guo, C.; Li, C.; Vu, H. V.; Hanna, P.; Lechtig, A.; Qiu, Y.; Mu, X.; Ling, S.; Nazarian, A.; Lin, S. J.; Kaplan, D. L., Thermoplastic molding of regenerated silk. Nature Materials 2020, 19 (1), 102-108.). ASN are then packed into predesigned mold, followed by hot pressing at 632 MPa and 125° C. for 15 min to generate silk bars.

As prepared silk fibroin (SF) bars were conjugated with amines of ethylene diamine (EDA) hydrochloride (Sigma-Aldrich, St. Louis, MO) by carbodiimide coupling in the presence of EDC (N-(3-Dimethylaminopropyl)-N'-ethyl carbodiimide) and NHS (N-Hydroxy Succinimide) (Sigma-Aldrich, St. Louis, MO). Briefly, SF bar (~200 mg) was treated in 0.1M MES (2-(N-morpholino) ethanesulfonic acid) buffer at pH 6. EDA (10×) was weighed and pre-dissolved in Ultrapure™ distilled water (Thermo-Fisher Scientific, Waltham, MA) and added to the SF bars. The pH was adjusted to 6 by dropwise addition of freshly prepared 1M sodium hydroxide (NaOH) solution. EDC (10×) and NHS (10×) were added to the reaction mixture at pH 6. The final MES buffer concentration of the reaction mixture was adjusted to 0.05M. The reaction was stirred at room temperature for 18 h, after which the remaining reaction solution was discarded and the EDA functionalized SF bars were washed in Ultrapure™ distilled water (20 mL, 30 min, 3×) to remove any unbound EDA from the SF bars. After washing, the aminated SF bars were dried at room temperature overnight and stored until further use.

Amine functionalized silk bars were placed in a 1.5 dram vial along with 5 mL of dry DMF. The solution was loaded on an orbital rotator for 20 min at 180 RPM. DMF was decanted, and bars are washed 3× with dry DCM over a glass frit (vacuum assembly with Buchner flask). The silk bars were then placed in a new 1.5 dram vial with a 5 mL solution of 0.1M C4 Iodonium Salt (0.33 g) in dry DCM. The reaction mixture was loaded on orbital rotating plate for 20 min at 180 RPM. After 20 min, the solution was decanted and replaced with 5 mL of 0.1M of 2,6-lutidine (0.057 mL) in dry DCM. The reaction mixture was loaded on orbital rotating plate for 20 min at 180 RPM. After 20 min, the DCM solution was decanted, and bars were soaked in DMF for ~30 seconds in a fritted funnel over a Buchner flask and vacuum assembly. After draining DMF with vacuum, the bars were washed 3× with dry DCM over the same glass frit assembly and placed in vials under high vacuum until further use.

Figure 10:
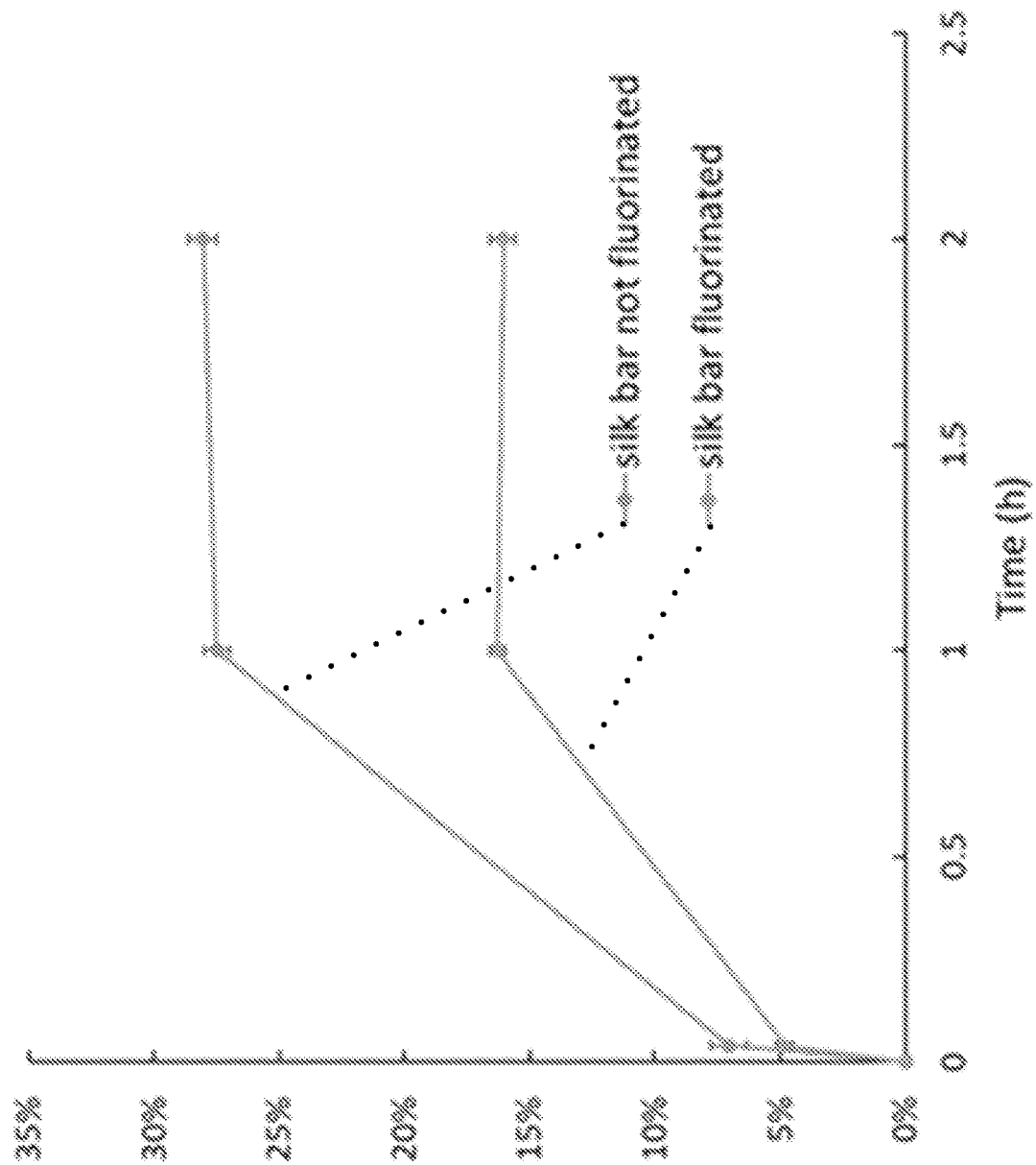
FIG. 10 is a plot of water uptake from silk fibroin bars with and without fluorination, as described in Example 2.

Referring to FIG. 10, a plot of the water uptake from the SF bars with and without fluorination is shown. The fluorinated SF bar had water uptake of 16% as compared with 28% for the non-fluorinated SF bar, while maintaining structural integrity.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A composition comprising:
a modified silk comprising one or more haloalkyl substituents; and
one or more linking agents, wherein each of the one or more linking agents couples a respective one of the one or more haloalkyl substituents to a respective amino acid of the modified silk.

2. The composition of claim 1, wherein the one or more haloalkyl substituents each comprises one or more halogen substituent selected from the group consisting of fluoro, bromo, chloro, and iodo.

3. The composition of claim 1, wherein the one or more haloalkyl substituents each comprises a structure of —$CxH_{0-2}R_{0-3}$, wherein:
R is a halo substituent selected from the group consisting of fluoro, chloro, bromo, and iodo; and
x ranges from 1 to 20 carbon atoms.

4. The composition of claim 3, wherein the carbon atoms form a linear chain.

5. The composition of claim 3, wherein x ranges from 1 to 10 carbon atoms.

6. The composition of claim 1, wherein the one or more linking agents covalently bonds the respective one of the one or more haloalkyl substituents to the respective amino acid.

7. The composition of claim 1, wherein each of the one or more linking agents comprises one or more chemical moiety to covalently bond the respective one of the one or more haloalkyl substituents to the respective amino acid.

8. The composition of claim 7, wherein the one or more chemical moiety includes a reaction product of an amino acid in the modified silk and one or more chemical moiety selected from the group consisting of a sulfonic acid group, a carboxylic acid group, an amine group, a ketone group, an alkyl group, an alkoxy group, a thiol group, a disulfide group, a nitro group, an aromatic group, an ester group, an amide group, and a hydroxyl group.

9. The composition of claim 7, wherein the one or more linking agents each comprises a diamine.

10. The composition of claim 8, wherein the one or more linking agents each is covalently bonded to a hydroxyl substituent in the amino acid in the modified silk fibroin, and wherein the one or more linking agents each comprises a structure of —$R_1(CO)(NR_2R_3)R_4(NR_5R_6)_X$, wherein:
$R_1$ comprises $C_1$-$C_6$ alkyl;
$R_2$ comprises a $C_1$-$C_{10}$ alkyl;
$R_3$ comprises hydrogen, a $C_1$-$C_{10}$ alkyl, or an aryl group;
$R_4$ comprises a $C_1$-$C_{10}$ alkyl;
$R_5$ comprises a $C_1$-$C_{10}$ alkyl;
$R_6$ comprises hydrogen or a $C_1$-$C_{10}$ alkyl; and
X comprises the haloalkyl substituent.

11. The composition of claim 1, the modified silk having one or more of the following properties:
(i) a water contact angle greater than 50°;
(ii) a halo content greater than 20 atomic percentage (at. %) as determined by X-ray photoelectron spectroscopy (XPS); and
(iii) a primary amine content less than 0.7 mM.

12. The composition of claim 1, wherein the modified silk has a water contact angle ranging from 50° to 150°.

13. The composition of claim 1, wherein the modified silk has a halo content ranging from 20 atomic percentage (at. %) to 50 at. % as determined by XPS.

14. The composition of claim 1, wherein the modified silk has a primary amine content ranging from 0.01 mM to 0.7 mM.

15. A method for making a modified silk having a predetermined hydrophobicity, the method comprising:
a) designing one or more haloalkyl substituents and selecting a substitution pattern of the one or more haloalkyl substituents in order to produce the predetermined hydrophobicity; and
b) making the modified silk having the substitution pattern of the one or more haloalkyl substituents.

16. A method for making a modified silk having a predetermined hydrophobicity, the method comprising:
a) selecting a substitution pattern of one or more haloalkyl substituents in order to produce the predetermined hydrophobicity; and
b) making the modified silk having the substitution pattern of the one or more haloalkyl substituents.

17. The composition of claim 1, wherein the modified silk has all of the following properties:
(i) a water contact angle greater than 50°;
(ii) a halo content greater than 20 at. % as determined by X-ray photoelectron spectroscopy (XPS); and
(iii) a primary amine content less than 0.7 mM.

18. The composition of claim 1, wherein the modified silk is a silk fibroin solution.

19. The composition of claim 1, wherein the modified silk is a solid form.

20. The composition of claim 1, wherein the modified silk is a modified silk fibroin.

* * * * *